US009820673B2

(12) United States Patent
Feldman et al.

(10) Patent No.: US 9,820,673 B2
(45) Date of Patent: *Nov. 21, 2017

(54) METHOD AND APPARATUS FOR MONITORING AN ORGAN OF A PATIENT

(71) Applicants: Marc D. Feldman, San Antonio, TX (US); John Porterfield, Edmond, OK (US); Karthik Raghavan, San Diego, CA (US); Jonathan W. Valvano, Austin, TX (US); John A. Pearce, Austin, TX (US)

(72) Inventors: Marc D. Feldman, San Antonio, TX (US); John Porterfield, Edmond, OK (US); Karthik Raghavan, San Diego, CA (US); Jonathan W. Valvano, Austin, TX (US); John A. Pearce, Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 232 days.

This patent is subject to a terminal disclaimer.

(21) Appl. No.: 14/213,473

(22) Filed: Mar. 14, 2014

(65) Prior Publication Data
US 2014/0257121 A1 Sep. 11, 2014

Related U.S. Application Data

(63) Continuation of application No. 12/657,832, filed on Jan. 28, 2010, now Pat. No. 8,706,219, which is a
(Continued)

(51) Int. Cl.
A61N 1/05 (2006.01)
A61B 5/053 (2006.01)
(Continued)

(52) U.S. Cl.
CPC ............ *A61B 5/0537* (2013.01); *A61B 5/029* (2013.01); *A61B 5/0295* (2013.01);
(Continued)

(58) Field of Classification Search
CPC ..... A61B 5/0537; A61B 5/0295; A61B 5/029; A61B 5/0476; A61B 5/0452;
(Continued)

(56) References Cited

U.S. PATENT DOCUMENTS 6,658,294 B1* 12/2003 Zadeh ...................... A61N 1/37
607/28
2008/0183072 A1* 7/2008 Robertson ............ A61B 5/1107
600/425

* cited by examiner

*Primary Examiner* — Rex R Holmes
(74) *Attorney, Agent, or Firm* — Ansel M. Schwartz

(57) ABSTRACT

An implanted device for an organ of a patient including a housing. The device includes a detector having electrodes that have a varying distance over time between them which produces a detector signal based on electrical signals derived from the organ. The device includes a signal processor disposed in the housing in communication with the detector which determines admittance from the detector signal based on the varying distance over time between the electrodes. The device includes a drive circuit disposed in the housing to cause the electrodes to generate emitted electrical signals. A method for monitoring a patient's organ.

6 Claims, 26 Drawing Sheets

Related U.S. Application Data continuation-in-part of application No. 12/086,040, filed as application No. PCT/US2006/047649 on Dec. 14, 2006.

(60) Provisional application No. 60/753,105, filed on Dec. 22, 2005.

(51) Int. Cl.

| | |
|---|---|
| *A61B 5/107* | (2006.01) |
| *A61B 5/20* | (2006.01) |
| *A61B 5/0452* | (2006.01) |
| *A61B 5/0476* | (2006.01) |
| *A61B 5/0488* | (2006.01) |
| *A61B 5/08* | (2006.01) |
| *A61B 5/029* | (2006.01) |
| *A61B 5/0295* | (2006.01) |
| *A61B 5/00* | (2006.01) |
| *A61B 5/0215* | (2006.01) |
| *A61N 1/365* | (2006.01) |
| *A61N 1/368* | (2006.01) |
| *A61N 1/39* | (2006.01) |

(52) U.S. Cl.
CPC .......... *A61B 5/0452* (2013.01); *A61B 5/0476* (2013.01); *A61B 5/0488* (2013.01); *A61B 5/0535* (2013.01); *A61B 5/0538* (2013.01); *A61B 5/0809* (2013.01); *A61B 5/1076* (2013.01); *A61B 5/204* (2013.01); *A61B 5/4878* (2013.01); *A61B 5/0031* (2013.01); *A61B 5/0215* (2013.01); *A61B 5/441* (2013.01); *A61B 5/4519* (2013.01); *A61N 1/3684* (2013.01); *A61N 1/36521* (2013.01); *A61N 1/3962* (2013.01)

(58) Field of Classification Search
CPC ... A61B 5/0809; A61B 5/0488; A61B 5/1076; A61B 5/0535; A61B 5/0538; A61B 5/204; A61B 5/4878; A61N 1/3962; A61N 1/3684
See application file for complete search history.

METHOD AND APPARATUS FOR MONITORING AN ORGAN OF A PATIENT

CROSS-REFERENCE TO RELATED APPLICATIONS

This is a continuation of U.S. patent application Ser. No. 12/657,832 filed Jan. 28, 2010, which is a continuation-in-part of U.S. patent application Ser. No. 12/086,040 filed Jun. 4, 2008, which is a 371 of international application PCT/US2006/47649 filed Dec. 14, 2006, which is an international application of U.S. provisional application Ser. No. 60/753,105 filed Dec. 22, 2005, all of which are incorporated by reference herein.

FIELD OF THE INVENTION

The present invention is related to determining tissue versus fluid components of an organ. (As used herein, references to the "present invention" or "invention" relate to exemplary embodiments and not necessarily to every embodiment encompassed by the appended claims.) More specifically, the present invention is related to determining tissue versus fluid components of an organ using electrodes having a varying inter-electrode distance to identify admittance. Moreover, the present invention is related to detecting a heart's volume or diameter via admittance of the heart. More specifically, the present invention is related to detecting a heart's volume or diameter via admittance of the heart and the use of a transmitter in communication with the detector which transmits a wireless signal indicative of the volume or the diameter of the heart via admittance of the heart. Patients with enlarged and weakened hearts are a particular group who will benefit from this invention

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Heart failure is one of the most common causes of admission to the hospital in the world. Studies have shown that patients with dilated hearts have a reduction in the frequency of hospital admission and prolongation of life with the implantation of bi-ventricular pacemakers and automatic implantable cardiac defibrillators (AICDs). This benefit extends to patients with both ischemic and idiopathic cardiomyopathy. Recently, "piggybacking" technology onto AICDs and bi-ventricular pacemakers for sensing the progression of impending HF to reduce the number and length of stay of hospital admissions for congestive heart failure has been proposed.

There are two proposed "piggybacked" heart failure warning systems placed on bi-ventricular pacemakers and AICDs to reduce hospital admissions. First, Chronicle® measures right heart pressures in an attempt to monitor increases that are indicative of heart failure. Second, Optivol® uses lung impedance (conductance) measurements as an indication of pulmonary edema. However, both are downstream measures of what is anticipated to be an earlier indicator of impending heart failure—left ventricular (LV) preload or left ventricular end-diastolic volume (LVEDV). There are currently no proposed technologies that can perform chronic left ventricular volume measurements in part because implanted devices in the left heart lead to arterial embolism and stroke.

Conductance measurements have been available as an invasive tool to detect instantaneous left and right ventricular volume since 1981. Conductance tetrapolar electrodes are usually placed on a catheter located within the heart chamber to determine instantaneous volume. Conductance systems generate an electric field using a current source, and volume is determined from the returning instantaneous voltage signal. Conductance electrodes have not been previously placed on the LV epicardium to interrogate the LV blood volume. Further, the conductance technique is limited as the resulting volume measured is a combination of both blood and surrounding myocardium, while only the blood volume is desired. The current invention proposes the use of an admittance measurement system, to separate the blood and muscle components from the combined voltage signal to determine LV preload from previously implanted AICD and bi-ventricular pacemakers, for the first time.

Thus, "piggybacking" the admittance measurement system described herein onto previously implanted AICD and bi-ventricular pacemakers will serve as an early warning system for impending heart failure, superior to the current approach of measuring right heart pressure and lung impedance (conductance).

LV Preload Determination:

LV preload may identify impending congestive heart failure in patients before increases in lung impedance (conductance) and right heart pressures occur. When the chronic canine model of congestive heart failure is acutely exposed to increases in afterload, an elevation of left but not right heart filling pressures has been shown to occur.

FIG. 1 is a bi-plane left ventriculogram from a patient with congestive heart failure and a previously implanted AICD/bi-ventricular pacer demonstrating how the leads span the LV blood from the lateral left ventricular epicardium to the right ventricular septum, and as an alternative configuration, from the lateral left ventricle to the right atrium (RA). These two lead configurations to be investigated are demonstrated in FIGS. 2a and 2b.

FIGS. 2a and 2b show two electrode configurations and include (a) LV septum to LV free wall, and (b) right atrium (RA) to distal LV free wall.

LV Preload as the Standard for Impending Heart Failure:

The backward heart failure concept was first proposed in 1832, and contends that when the LV fails to discharge its contents, blood accumulates and pressures rise in the atrium and venous system emptying into it. The inability of the LV to shorten against a load alters the relationship between end-systolic pressure and volume so that LV end-systolic volume rises. The following sequence then occurs, which at first maintains cardiac output, but ultimately leads to clinical deterioration—(a) LV end diastolic volume and pressure increase, (b) the volume and pressure rise in the left atrium, (c) the left atrium contracts more vigorously (Starling's Law), (d) the pressure in the pulmonary veins and capillary beds behind the LV rise, (e) transudation of fluid from the pulmonary capillary beds into the pulmonary interstitial space increases, (f) the elevation of LV, left atrial, and pulmonary venous pressures results in backward transmission of pressures into the pulmonary arterial circuit and leads to pulmonary hypertension, and finally, (g) right heart failure then occurs as a consequence of left heart failure.

Further, as the LV fails, it will remodel to accommodate the increased load, to reduce chamber pressures. Increased LV preload is more easily detected than pressure elevation since the diastolic pressure-volume relation is relatively flat and produces a larger change in volume for a given change in pressure. This relationship is more evident as the LV remodels and dilates since the diastolic ventricular pressure-volume relation flattens in heart failure. An increase in preload will also antedate an elevation in right heart systolic pressures, due to the length-tension relationship of cardiac muscle, i.e.,—muscle is stretched before generating greater systolic pressures. Based on these additional arguments, the principal investigator and colleagues anticipate that increasing LV preload will be the most sensitive measure of impending congestive heart failure.

Right Heart Pressure Measurement:

The Chronicle® device utilizes a pressure sensor placed on the right ventricular lead to detect when there is an increase in right heart pressures to warn of impending congestive heart failure. The device has been validated against invasive fluid filled pressure sensors up to 1 year, in a variety of positions (supine and sitting) and activities (valsalva and exercise). Pressure increases have been shown to occur in 9 of 12 patients proceeding hospitalization for congestive heart failure, and there was a trend in fewer heart failure admissions with the pressure monitoring intervention compared to a control group in the COMPASS-HF study.

However, there are many concerns regarding using right heart pressures to monitor for impending heart failure. The major concern is that right heart failure is downstream of left heart failure and pulmonary edema, and based on physiologic principles, will be a less robust measure. Evidence of this concern is that Chronicle® was only able to detect 9 of 24 events that were treated with the adjustment of heart failure medications to avoid hospitalization. Second, the device was reviewed by the FDA in February 2007, and approval was not granted based on the COMPASS-HF study due to statistically non-significant results between right heart pressure and control arms. Third, the device requires correction for varying ambient atmospheric pressure with an external device that records ambient barometric pressure.

Left Atrial Pressure Measurement:

There are currently two groups developing implantable left atrial (LA) pressure sensors to warn of impending congestive heart failure. The first is Savacor which has developed HeartPOD™ sensor, and is currently engaged in the Homeostasis 1 Clinical Trial. The second group is a collaboration between Virginia Commonwealth University and Vital Sensors based in Richmond, Va.

The concern regarding this technology is that there have been patients in the Homeostasis 1 Clinical Trial who have had strokes, due to the presence of a pressure sensor implanted on the LA side of the intra-atrial septum. In contrast, our approach of using epicardial Admittance does not implant an intra-cardiac foreign device in the left heart chambers, and thus there is no increased risk of stroke.

Lung Impedance (Conductance):

The Optivol® is implemented in the InSync Sentry pacemakers made by Medtronic, Inc. The operating principle involves showing when the fluid index has passed a certain threshold from baseline, thus showing an increase in "lung wetness". OptiVol uses a trans-thoracic resistance measurement from the tip of the RV AICD lead to the case of the battery pack for the pacemaker/defibrillator, and thus provides a wide electric field including the LV, LA, thoracic skeletal muscle, ipsilateral lung tissue, intravascular lung volume, and finally pulmonary interstitial edema to measure a changing fluid index.

When Optivol® was initially investigated in 33 patients, a promising 77% sensitivity with only 1.5 false-positive per year were described. However, a larger series of 373 patients revealed a less impressive sensitivity of 60% for heart failure detection, with a positive predictive value of 60% as well. The explanation for the decreasing sensitivity and positive predictive value of Optivol® is consistent with the wide variety of tissues being interrogated by the electric field. For instance, factors that would decrease the impedance measurement include pulmonary interstitial congestion (the only true endpoint), increased myocardial mass, increased intra-vascular blood volume, pulmonary effusions, and edema near the AICD pocket. In contrast, factors that would increase and thus reduce the sensitivity of the impedance measurement include alterations in pulmonary tissue due to heart failure, which include increased small airway resistance, increased air volume in the lung, previous smoking with COPD, increased lymphatic drainage, and reduced skeletal muscle mass as part of cardiac cachexia. Finally, since the authors of this patent application anticipate that increased pulmonary interstitial edema occurs following increased LV end-diastolic volume, a pure measure of LV preload will achieve more favorable sensitivity and specificity of heart failure detection. Currently no such device exists.

A second criticism is that Optivol® utilizes state-of-the-art conductance-to-volume equations which assume the distance between the stimulation and voltage sensing electrodes are constant. This is not the case with Optivol®, where the RV AICD lead electrodes are in motion as a source electrode with the relatively stationary AICD generator. Thus, Optivol® is currently being used for measurements where the independent electrodes may have arbitrary, time-dependent distances from one another. However, the implications of violating Baan's assumptions which assume fixed electrode positions have not been addressed. This raises the question of the sensitivity of the measurement to electrode positioning. The new approach proposed in the current application is based upon motion of source and sink electrodes and can be used to improve the accuracy of the Optivol® approach.

Inadequate Traditional Conductance Measurements:

Traditionally, volume measurements are made by determining the time dependent (as the heart beats) value of conductance using a catheter placed in the left ventricle. The original theory was proposed by Jan Baan in 1981 and relates conductance to volume through a simple equation based on stroke volume, resistivity of blood, and the length between the voltage contacts of the catheter.

$$\text{Volume} = \frac{\rho L^2}{\alpha}(G_{blood} - G_{\|}),$$

where $\rho$ represents the resistivity of blood, L represents the fixed length between the voltage contacts, $\alpha$ is constant dependent on the stroke volume (Baan assumed it to be 1), $G_{blood}$ is the conductance of blood, and $G_{\|}$ is the muscle conductance in parallel with the blood.

There are several criticisms of this traditional method. The first is that the relationship between blood conductance and volume is not linear, as shown in the literature, and as implied by the non-uniform shape of the stimulating field. Second, the measurement not only extends into the blood pool, but also into the surrounding tissues (such as the myocardium). This implies that the measurement will artifactually increase the volume because the catheter will see further than only the blood pool. The correction for the parallel Z conductance $G_{\parallel}$ is a calculated constant in the above equation, but the parallel conductance is known to be time-varying. The accepted methods for conductance measurement are outdated in this matter. For example, the Fick method is used with the Conductance technique to measure the steady state parallel conductance using a hypertonic saline bolus injection. The value derived from this measurement is a constant, and is not time dependent. Thus, there is a need to mature this approach to separate the blood and muscle components of the signal. The authors of this patent application are the first to develop a real-time method to distinguish between blood and muscle components using admittance measurements.

FIG. 3a shows incomplete traditional conductance circuit approach that models both cardiac muscle ($G_m$) as real or conductive components only. FIG. 3b shows a circuit model including the imaginary or capacitive properties of cardiac muscle.

Finally, the volume-conductance equation is modeled after an incomplete circuit (FIG. 3a). Measurements were considered all real because only the magnitude was measured. However, such an approach ignores the imaginary or capacitive properties of cardiac muscle (FIG. 3b), and thus separating blood and muscle is difficult and done incorrectly using this traditional approach.

Moreover, currently, there are no heart failure warning systems which can detect the left ventricular volume or left ventricular diameter, since any instrumentation placed within the left heart would lead to clot formation and a subsequent stroke. A technique has been developed to piggyback electrodes onto the surface of the heart to mitigate against the risk of stroke, while still determining when the left ventricle begins to dilate as a means to warn of impending heart failure. For this device to be effective, the patient and doctor need a technique to allow the left ventricular volume and/or diameter information to be transmitted. One such technique would be telemetry—a technology that allows remote measurement and reporting of information on the left ventricular volume or diameter, or a change in left ventricular volume of diameter from baseline. Remote reporting of this information will allow the patient to report this information to his/her doctor from a site other than the physician's office, such as home.

BRIEF SUMMARY OF THE INVENTION

The present invention pertains to an apparatus for determining tissue versus fluid components of an organ. The apparatus comprises a detector that generates a detector signal based on electrical signals derived from tissue and fluid. The apparatus comprises a signal processor in communication with the detector which subtracts in real time a tissue component from the detector signal and produces a fluid volume signal.

The present invention pertains to a method for monitoring a patient's fluid volume of a patient's organ. The method comprises the steps of producing with a detector a signal based on electrical signals derived from tissue and fluid of the organ. There is the step of subtracting with a signal processor in communication with the detector a tissue component from the detector signal to produce a fluid volume signal.

The present invention pertains to an apparatus for monitoring a patient's organ. The apparatus comprises a detector having electrodes that have a varying distance between them which produces a detector signal based on electrical signals derived from the organ. The apparatus comprises a signal processor in communication with the detector which determines admittance from the detector signal based on the varying distance between the electrodes.

The present invention pertains to a method for monitoring a patient's organ. The method comprises the steps of producing a detector signal from a detector having electrodes that have a varying distance between them based on electrical signals derived from the organ. There is the step of determining admittance from the detector signal with a signal processor in communication with the detector based on the varying distance between the electrodes.

The present invention pertains to an AICD/BI-V Pacemaker for a heart of a patient. The AICD/BI-V pacemaker comprises a housing. The AICD/BI-V Pacemaker comprises a first and second electrode configured to be disposed in the right ventricular (RV) septum of the heart. The AICD/Bi-ventricular Pacemaker comprises a catheter having a third and fourth electrode that is configured to extend from the housing into the coronary sinus of the heart, and extended into a lateral coronary vein of the heart. The AICD/Bi-ventricular Pacemaker comprises a current source disposed in the housing to cause the electrodes to generate emitted electrical signals. The AICD/Bi-ventricular Pacemaker comprises a transmitter disposed in the housing that transmits received signals from the electrodes after the emitted signals have passed through the heart.

The present invention pertains to an apparatus for monitoring an organ of a patient. The apparatus comprises a detector which detects the Admittance of the organ. The apparatus comprises a transmitter in communication with the detector which transmits a wireless signal indicative of the admittance of the organ.

The present invention pertains to a method for monitoring an organ of a patient. The method comprises the steps of detecting with a detector the admittance of the organ. There is the step of transmitting with a transmitter in communication with the detector a wireless signal indicative of the admittance of the organ.

BRIEF DESCRIPTION OF THE SEVERAL VIEWS OF THE DRAWING

In the accompanying drawings, the preferred embodiment of the invention and preferred methods of practicing the invention are illustrated in which.

DETAILED DESCRIPTION OF THE INVENTION

Figure 2A:
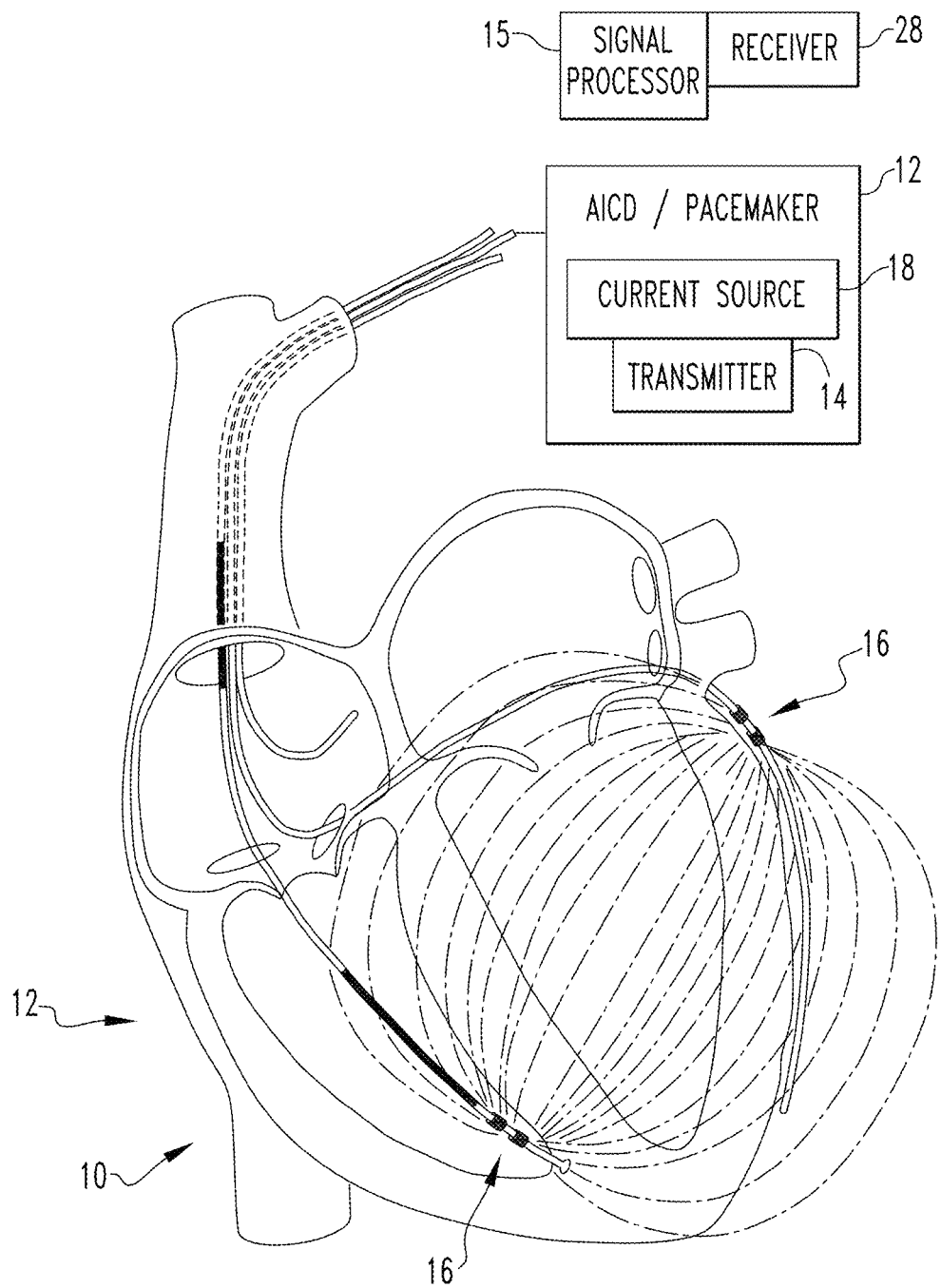
FIGS. 2a and 2b show two electrode configurations and include (a) RV septum to LV free wall, and (b) right atrium (RA) to distal LV free wall.
Figure 2B:
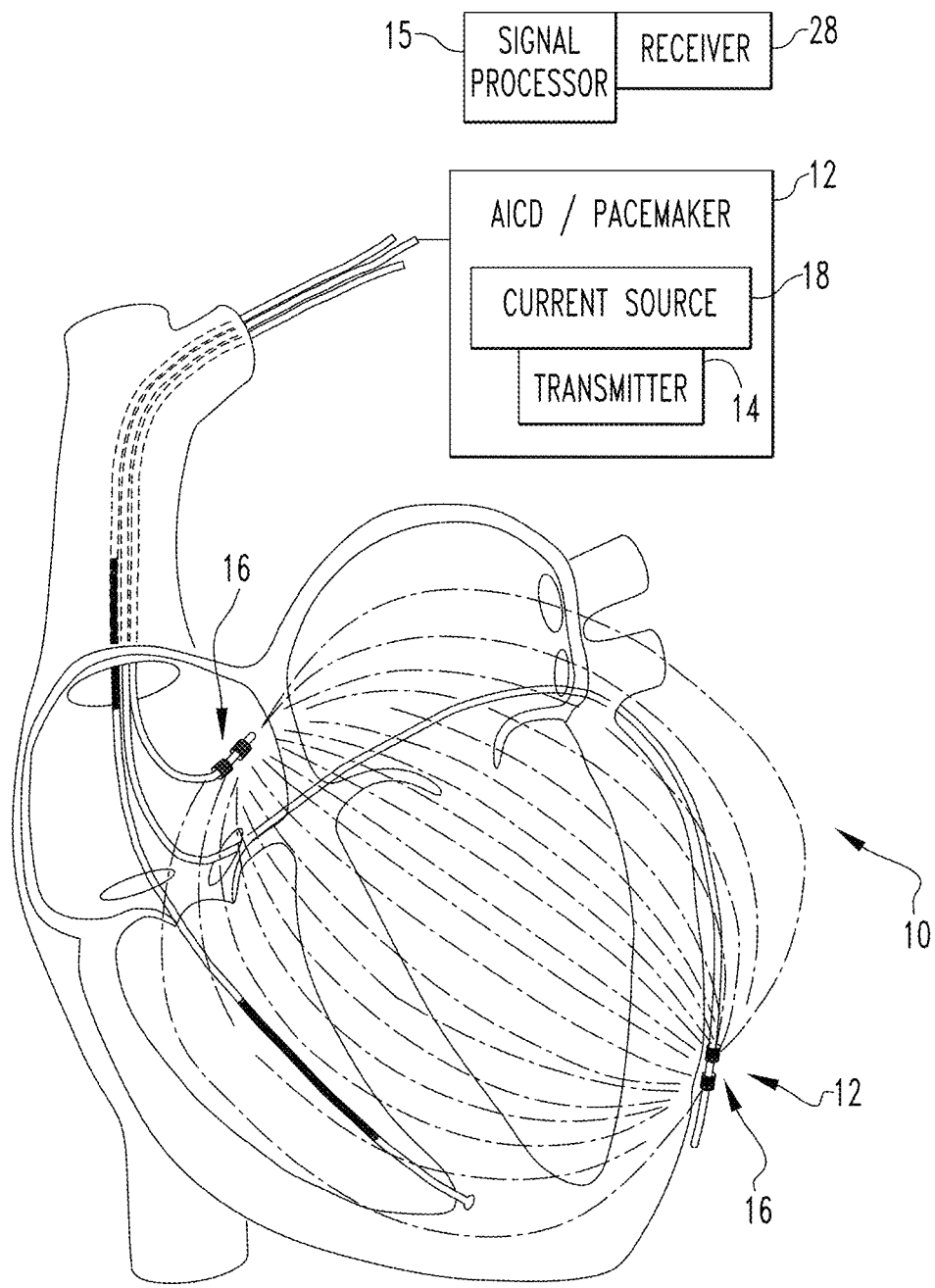

Referring now to the drawings wherein like reference numerals refer to similar or identical parts throughout the several views, and more specifically to FIGS. 2a and 2b thereof, there is shown an apparatus 10 for determining tissue versus fluid components of an organ. The apparatus 10 comprises a detector 12 that generates a detector signal based on electrical signals derived from tissue and fluid. The apparatus 10 comprises a signal processor 15 in communication with the detector 12 which subtracts in real time a tissue component from the detector signal and produces a fluid volume signal.

The detector 12 may include a plurality of electrodes 16 adapted to contact the organ that produce a combined signal that has the tissue component and a fluid component. The electrodes 16 may have a varying distance between them and the processor 15 determines organ surface admittance based on the vary distance between the electrodes 16. The organ may be a heart, the fluid is blood, the tissue is myocardium and the processor 15 determines LV, RV, LA, or RV area of the heart in 1, 2 or 3 dimensions. For instance, with the heart, an increasing blood volume is indicative of heart failure.

The myocardial component Rm may be determined by $$R_m = \frac{-\text{Im}\{\bar{Z}\} \times \left(1 + \left(\frac{\omega \varepsilon_m}{\sigma_m}\right)^2\right)}{\frac{\omega \varepsilon_m}{\sigma_m}},$$

where $\bar{Z}$ is the complex impedance; $\omega=2\pi f$ where f is the frequency; $\varepsilon_m$ is permittivity of muscle; and $\sigma_m$ is the conductivity of muscle. The fluid may be blood and blood component Rb may be determined by $$R_b = \text{Re}\{\bar{Z}\} - \frac{R_m}{1 + (\omega R_m C_m)^2},$$

where $\bar{Z}$ is the complex impedance; $\omega=2\pi f$ where f is the frequency; $R_m$ is the resistance of muscle, and $C_m$ is the capacitance of muscle. The signal processor 15 may subtract in real time the myocardial component from the detector signal and produce the left and right ventricle, and left and right atrial blood volume signal.

The present invention pertains to a method for monitoring a patient's fluid volume of a patient's organ. The method comprises the steps of producing with a detector 12 a detector signal based on electrical signals derived from tissue and fluid of the organ. There is the step of subtracting with a signal processor 15 in communication with the detector 12 a tissue component from the detector signal to produce a fluid volume signal.

The detector 12 may include a plurality of electrodes 16 adapted to contact the organ and the producing step may include the step of producing a combined signal from the electrodes 16 that has the tissue component and a fluid component. The electrodes 16 may have a varying distance between them and there can be the step of the processor 15 determining admittance based on the varying distance between the electrodes 16. There may be the step of the processor 15 determining an LV spatial measurement in 1, 2 or 3 dimensions of the heart.

There may be the step of the processor 15 determines myocardial component Rm by $$R_m = \frac{-\text{Im}\{\overline{Z}\} \times \left(1 + \left(\frac{\omega \varepsilon_m}{\sigma_m}\right)^2\right)}{\frac{\omega \varepsilon_m}{\sigma_m}},$$

where $\overline{Z}$ is the complex impedance; $\omega = 2\pi f$ where f is the frequency; $\varepsilon_m$ is permittivity of muscle; and $\sigma_m$ is the conductivity of muscle. There can be the step of the processor 15 determines a blood component Rb by $$R_b = \text{Re}\{\overline{Z}\} - \frac{R_m}{1 + (\omega R_m C_m)^2},$$

where $\overline{Z}$ is the complex impedance; $\omega = 2\pi f$ where f is the frequency; $R_m$ is the resistance of muscle, and $C_m$ is the capacitance of muscle. There may be the step of the signal processor 15 subtracting in real time the myocardial component from the detector signal and produces the left ventricle blood volume signal.

The present invention pertains to an apparatus 10 for monitoring a patient's organ. The apparatus 10 comprises a detector 12 having electrodes 16 that have a varying distance between them which produces a detector signal based on electrical signals derived from the organ. The apparatus 10 comprises a signal processor 15 in communication with the detector 12 which determines admittance from the detector signal based on the varying distance between the electrodes 16.

The present invention pertains to a method for monitoring a patient's organ. The method comprises the steps of producing a detector signal from a detector 12 having electrodes 16 that have a varying distance between them based on electrical signals derived from the organ. There is the step of determining admittance from the detector signal with a signal processor 15 in communication with the detector 12 based on the varying distance between the electrodes 16.

The organ can be a lung and the producing step includes the step of producing the detector signal from the detector 12 having electrodes 16 that have a varying distance between them based on electrical signals derived from the lung to separate the fluid and lung tissue components to determine pulmonary edema. The organ can be a bladder and the producing step includes the step of producing the detector signal from the detector 12 having electrodes 16 that have a varying distance between them based on electrical signals derived from the bladder to separate the urine and bladder wall components to determine when the bladder is full. The organ can be a brain and the producing step includes the step of producing the detector signal from the detector 12 having electrodes 16 that have a varying distance between them based on electrical signals derived from the brain to separate central nervous system fluid (CSF) from the brain tissue as a measure of brain edema.

The organ can be a skeletal muscle and the producing step includes the step of producing the detector signal from the detector 12 having electrodes 16 that have a varying distance between them based on electrical signals derived from the skeletal muscle to separate the blood and edema components from tissue properties of skeletal and smooth muscle to determine blood vessel and skeletal muscle edema. The organ can be epidermis and the producing step includes the step of producing the detector signal from the detector 12 having electrodes 16 that have a varying distance between them based on electrical signals derived from the epidermis to differentiate dermis from epidermis from blisters in regard to skin burns.

The present invention pertains to an AICD/Bi-ventricular Pacemaker 25 for a heart of a patient. The AICD/Bi-ventricular pacemaker 25 comprises a housing. The AICD/Bi-ventricular Pacemaker 25 comprises a first and second electrode configured to be disposed in the right ventricular (RV) septum of the heart. The AICD/Bi-ventricular Pacemaker 25 comprises a catheter having a third and fourth electrode that is configured to extend from the housing into the coronary sinus extending into a lateral wall vein of the heart. The AICD/Bi-ventricular Pacemaker 25 comprises a current source 18 disposed in the housing to cause the electrodes 16 to generate emitted electrical signals. The AICD/Bi-ventricular Pacemaker 25 comprises a transmitter 14 disposed in the housing that transmit received signals from the electrodes 16 after the emitted signals have passed through the heart and interacted with the heart.

Figure 1:
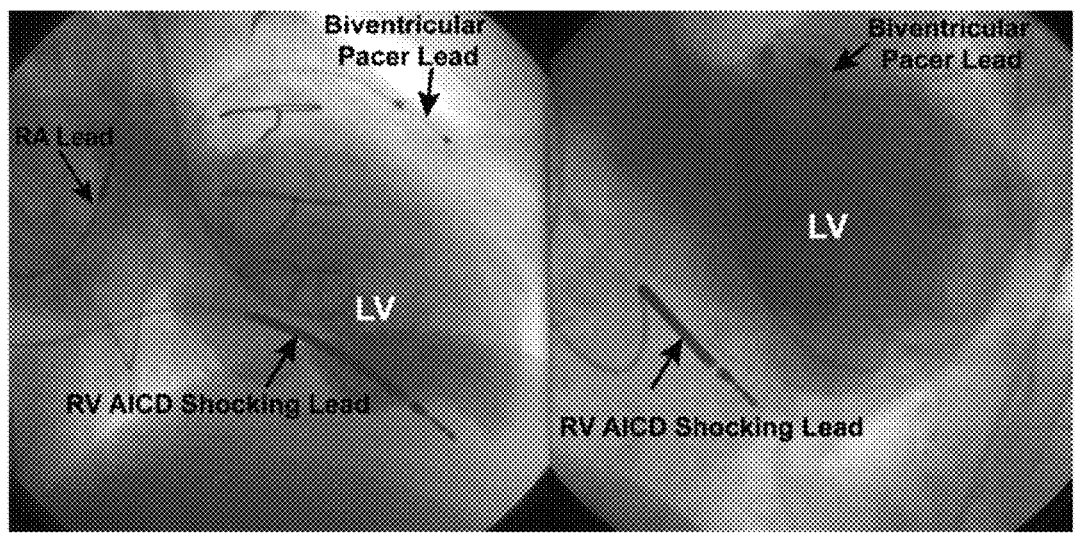
FIG. 1 is a bi-plane left ventriculogram from a patient with congestive heart failure and a previously implanted AICD/bi-ventricular pacer demonstrating how the leads span the LV blood from the lateral epicardium to the right ventricular septum, and alternatively from the lateral epicardium to the right atrium (RA). These two lead configurations described above are demonstrated in FIGS. 2a and 2b.
Figure 3A:
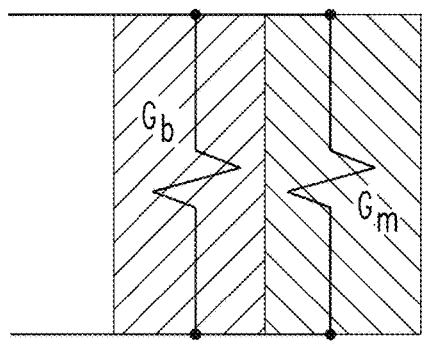
FIG. 3a shows an incomplete traditional conductance circuit approach that models both cardiac muscle ($G_m$) as real or conductive components only.
Figure 3B:
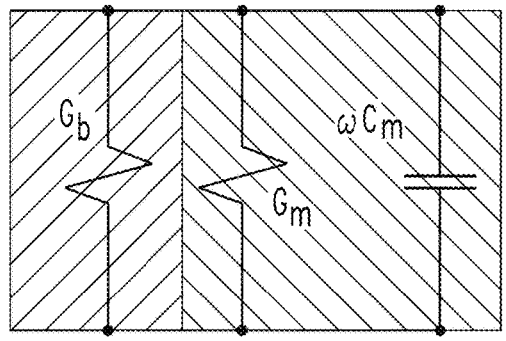
FIG. 3b shows realistic circuit including the imaginary or capacitive properties of cardiac muscle.

In the operation of the invention, the present invention proposes to solve the problem stated above by "piggybacking" the admittance measurement system, onto currently deployed bi-ventricular and AICD leads, to electrically detect either true LV preload, or an increase in LV preload from baseline. Bi-ventricular and the RV AICD leads are already located in the ideal locations—the lateral LV epicardium and the right ventricular (RV) septum. Since blood has lower resistivity than myocardium, the preferential path for a substantial fraction of the current flow will be the LV blood volume (see FIGS. 1 & 2). To improve upon conductance theory, the concept of a complex plane measurement of admittance (Y) is introduced, to replace the concept of the magnitude-only conductance measurement. This technique makes use of the native capacitive properties unique to muscle to identify its contribution to the measured signal so that it can be removed in real-time without the need for hypertonic saline injection. The basis of measuring admittance instead of conductance is that at frequency ranges of around f=20 kHz ($\omega = 2\pi f$ r/s), blood is purely resistive and has no measurable capacitance, but muscle has both capacitance and resistance properties (FIG. 3b). This fact allows separation of the admittance of the muscle from the combined admittance, using electric field theory.

For a vector electric field, E, in homogeneous tissue the conductance and capacitance between the electrodes 16 that establish the field are given by:

$$G = \frac{I}{V} = \frac{\iint_S \sigma E \cdot dS}{-\int_b^a E \cdot dL} = \sigma F \quad C = \frac{Q}{V} = \frac{\iint_S \varepsilon E \cdot dS}{-\int_b^a E \cdot dL} = \varepsilon F \quad [1]$$

where: G=conductance (S), I=current (A), V=voltage (V), σ=electrical conductivity (S/m), F=the field geometry factor (m), C=capacitance (F), and Q=charge (C). The integration is from one electrode to the other along a vector pathway, L, and the surface, S, encloses all of the current from the source electrode. For homogeneous tissue the measured conductance and capacitance are related by a simple ratio: G=C σ/∈.

Figure 4A:
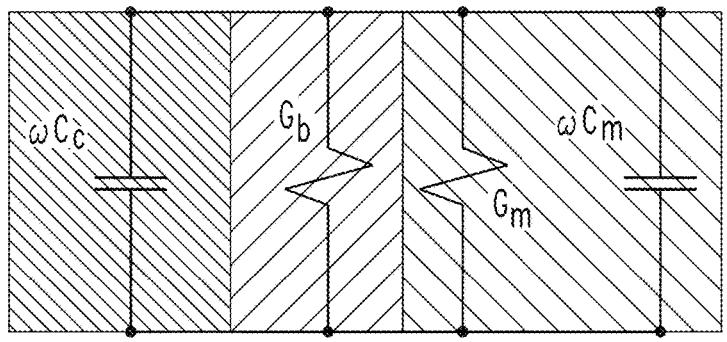
FIGS. 4a and 4b show a new proposed circuit model (a) which models the blood ($G_b$) as resistive, the cardiac muscle as both resistive ($G_m$) and capacitive ($\omega C_m$), and also takes into account any capacitive properties of the measuring catheters ($\omega C_c$). The measured complex admittance, $Y=G_b+G_m+j\omega(C_c+C_m)$ (b). The angular frequency, $\omega=2\pi f$, with f in (Hz).
Figure 4B:
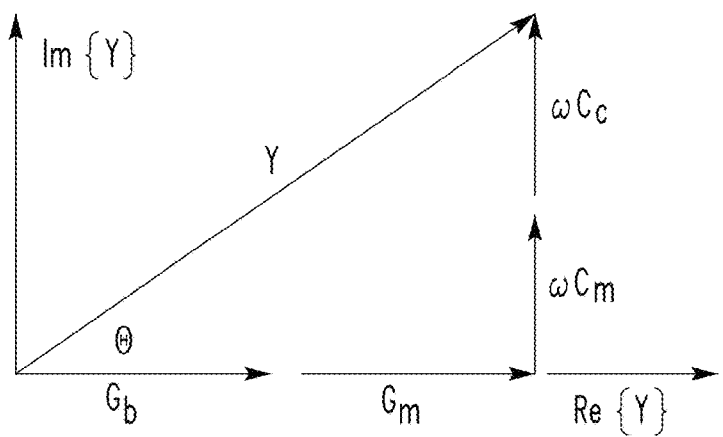

FIGS. 4a and 4b show a new proposed circuit model (a) which models the blood ($G_b$) as resistive, the cardiac muscle as both resistive ($G_m$) and capacitive ($\omega_m$), and also takes into account any capacitive properties of the measuring catheters ($\omega C_c$). The measured complex admittance (b), $Y=G_b+G_m+j\omega(C_c+C_m)$. The angular frequency, $\omega=2\pi f$, with f in (Hz).

The model in FIG. 4a includes parasitic capacitances between the wires in the catheter, $C_c$, and also capacitance in the signal due to the cardiac muscle, $C_m$. Blood has conductive properties only, $G_b$. The total measured complex admittance, Y, (FIG. 4b) combines blood and muscle components with catheter effects. In practice, the magnitude, |Y|, and phase angle, θ, of the complex admittance are measured. From these, the real part, $Re\{Y\}=G_b+G_m=|Y|\cos(\theta)$, and imaginary part, $Im\{Y\}=\omega(C_c+C_m)=|Y|\sin(\theta)$, are found. $C_c$ and the large-volume field form factor, $F_\infty$, are measured for the catheters in saline as part of the calibration procedure. $C_m$ is found by subtraction using the imaginary part of Y, and then $G_m=\sigma_m/\in_m C_m$. The electrical conductivity and permittivity of tissue, $\sigma_m$ and $\in_m$, for the organ of interest may be used to complete this calculation.

Measurements presented by Gabriel et al. (C. Gabriel, S. Gabriel, and E. Corthout, "The dielectric properties of biological tissues: I. literature survey." *Phys Med Biol*, vol. 41, no. 11, pp. 2231-2249, November 1996; S. Gabriel, R. W. Lau, and C. Gabriel, "The dielectric properties of biological tissues: II. measurements in the frequency range 10 Hz to 20 GHz." *Phys Med Biol*, vol. 41, no. 11, pp. 2251-2269, November 1996) show a relative permittivity for muscle in excess of 15,000 at the proposed frequency of operation (20 kHz). The permittivity of blood is dominated by the water content, and would measure in the neighborhood of 70 if it could be separated from the "admittivity", $\psi=\sigma+j\omega\in_0\in_r$ (S/m), because the water is the only source of dipole moment in blood (permittivity is a measure of the dipole moment per unit volume, i.e., the ability of a material to store electrical energy in an electric field). The measurements on blood show that the imaginary part of admittivity, ψ, is not measurable in blood; i.e., $\sigma>>\omega\in_0\in_r$. On this point the Gabriel et al. data disagree. Unfortunately, they have chosen to include conductivity effects in with the permittivity; i.e., ∈ is complex and includes a term $j\sigma/\omega\in_0$, and their reported high numbers for blood are actually dominated by the conductivity effects. These two electrical properties are separated out because they arise from different physical phenomena (conductivity from the net translational motion of free charge and permittivity from rotational motion of bound charge) and it is important to the measurements to do so. The result is that at 20 kHz we are able to measure a significant phase angle in the admittance, Y (S), and this is the fundamental observation that we use in our new technique.

The utility of the new technique is that it obviates the need for hypertonic saline injection, or comparable parallel conductance measurement. In addition, the parallel muscle conductance is traditionally subtracted as a constant in traditional conductance measurement techniques, but it has shown that the muscle wall moves in and out of the stimulation field applied as the heart beats, so it is incorrect to assume the parallel conductance is a constant. The contribution of muscle can be subtracted regardless of orientation of the catheters, size of the heart, or variability within the heart cycle in real time using the admittance technique.

Figure 5A:
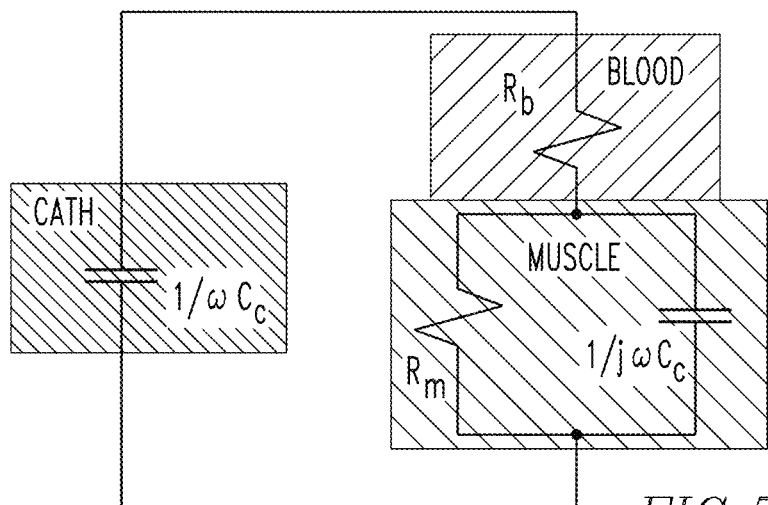
FIG. 5a shows the electrical model of the measurement required to separate the muscle component from the blood component where epicardial placement of the admittance electrodes is shown.
Figure 5B:
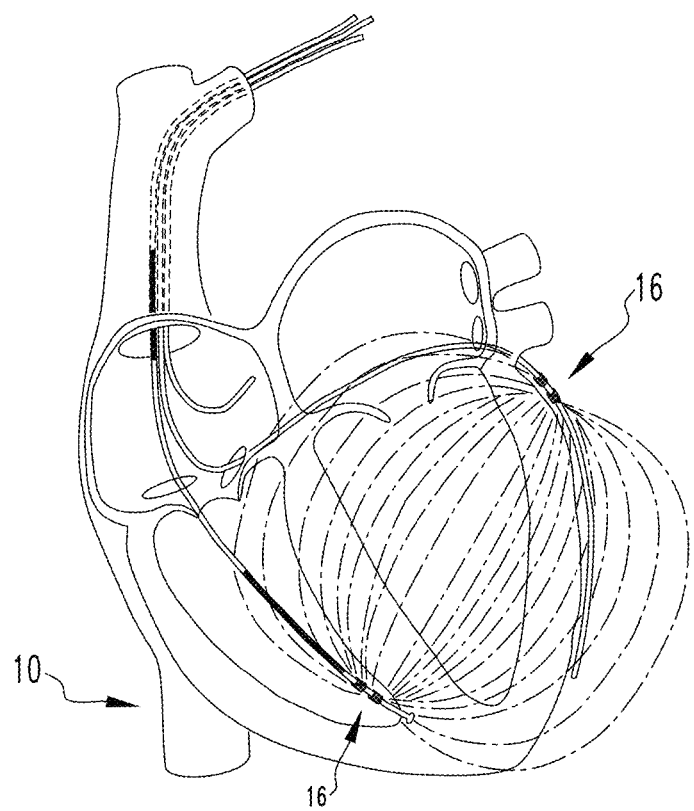
FIG. 5b shows simulation of an AICD/bi-ventricular pacemaker upon which the circuit diagram is based.

An electrical model of the measurement is required to provide a means of separating the muscle component from the blood component with epicardial placement of the admittance electrodes 16. A traditional conductance catheter model with fixed electrodes 16 uses a parallel combination of $G_b$, $G_m$, and $j\omega C_m$ which forms the complex admittance $Y=G_b+G_m+j\omega C_m$. However, because the epicardial admittance leads are in constant motion with the systolic and diastolic movement of the heart, the new measurement is substantially different. Thus, a new model is developed below. For mathematical convenience, it is formulated using impedance, Z, where Z=1/Y. FIG. 5B displays that as the stimulation current passes from an electrode placed on the LV free wall epicardium (as part of the bi-ventricular pacer), then through the blood, then through the septum, the different layers can be approximated as the boundaries between homogenous tissues of specific electrical impedance. For example, it is known blood produces no phase shift at frequencies of 20 kHz, it can be represented as a single resistance, or $R_b$ (FIG. 5A). Additionally, because muscle has both capacitance and resistance, it can be represented as a resistor and a capacitor in parallel, $R_m$, and $1/\omega C_m$, as shown in FIG. 5A. The circuit model assumes that the stimulation current flows through a combination of blood and muscle in series, and capacitive and resistive properties of muscle in parallel, and is described in equation [6]. The circuit model is valid because the conductivity of blood is about 3 times higher than the conductivity of muscle, making the series path through the blood pool preferable for the majority of the current field. Because the current passes through a muscle layer twice (LV free wall and septum), and these muscle layers are in series, they can be represented by only one equivalent resistance and capacitance.

FIG. 5a shows the electrical model of the measurement required to separate the muscle component from the blood component with epicardial placement of the admittance electrodes 16 is shown. FIG. 5b shows simulation of an AICD/bi-ventricular pacemaker upon which the circuit diagram is based.

Impedance (Z) Separation of Blood and Muscle Components.

The circuit model shown in FIG. 5a can be mathematically displayed as Equation [6], where: Z=complex impedance (Ω), $R_b$=blood resistance (Ω), $R_m$=cardiac muscle resistance (Ω), $C_c$=catheter capacitance (F), and $C_m$=cardiac muscle capacitance (F), j=square root of −1, and $\omega=2\pi f$ (f=frequency, or 20 kHz).

$$\bar{Z} = \frac{1}{j\omega C_c} \left\| \left( R_b + R_m \| \frac{1}{j\omega C_m} \right) \right. \quad [6]$$

and ∥ means that the two quantities add in parallel, or $$a\|b = \left(\frac{1}{a} + \frac{1}{b}\right)^{-1} \quad [7]$$

$$= \frac{1}{j\omega C_c} \left\| \left( R_b + \frac{\frac{R_m}{j\omega C_m}}{R_m + \frac{1}{j\omega C_m}} \right) \right.$$

$$= \frac{1}{j\omega C_c} \| \left( R_b + \frac{R_m}{j\omega R_m C_m + 1} \times \left( \frac{1 - j\omega R_m C_m}{1 - j\omega R_m C_m} \right) \right)$$

$$= \frac{1}{j\omega C_c} \| \left( R_b + \frac{R_m - j\omega R_m^2 C_m}{1 + (\omega R_m C_m)^2} \right)$$

$$= \frac{1}{j\omega C_c} \| \left( R_b + \frac{R_m}{1 + (\omega R_m C_m)^2} - j \frac{\omega R_m^2 C_m}{1 + (\omega R_m C_m)^2} \right).$$

To separate the blood and muscle components in a traditional conductance catheter tetrapolar measurement, a calibration is performed to determine the amount of phase contribution from the catheter capacitance ($C_c$) for varying conductivity solutions, and remove it. However, in the epicardial Admittance measurement there is also a varying length between the current carrying electrodes 16 that complicates the issue of calibration. For the preliminary derivation, it is assumed $C_c$ to be small in Equation [7], allowing its impedance $1/(j\omega C_c)$ to be large in the parallel combination (and therefore neglected).

Therefore, assuming $C_c$ to be small, making the parallel combination mostly dependent on the blood and tissue, Equation [7] becomes:

$$\bar{Z} = \left( R_b + \frac{R_m}{1 + (\omega R_m C_m)^2} - j \frac{\omega R_m^2 C_m}{1 + (\omega R_m C_m)^2} \right), \quad [8]$$

$$\text{Im}\{\bar{Z}\} = \frac{-\omega R_m^2 C_m}{1 + (\omega R_m C_m)^2}$$

Using the conductance/capacitance relationship in Equation [8] to separate $C_m$ from $R_m$, $$C_m = \frac{\varepsilon_m}{R_m \sigma_m}; \quad \text{Im}\{\bar{Z}\} = \frac{-R_m \frac{\omega \varepsilon_m}{\sigma_m}}{1 + \left(\frac{\omega \varepsilon_m}{\sigma_m}\right)^2} \quad [9]$$

Rearranging, $$R_m = \frac{\text{Im}\{\bar{Z}\} \times \left(1 + \left(\frac{\omega \varepsilon_m}{\sigma_m}\right)^2\right)}{\frac{\omega \varepsilon_m}{\sigma_m}} \quad [10]$$

The imaginary part of $\bar{Z}$ is negative, making $R_m$ positive. Then, $$R_b = \text{Re}\{\bar{Z}\} - \frac{R_m}{1 + (\omega R_m C_m)^2} \quad [11]$$

The procedure for calculating the separated blood and muscle resistances follows the derivation above.

1. Determine from a separate surface probe experiment (26) what the values of $\varepsilon_m$ and $\sigma_m$ are to use in Equation 9.
2. Find the real and imaginary parts of the measurement using $$Re\{\bar{Z}\} = |\bar{Z}| \cos(\theta)$$

and $$Im\{\bar{Z}\} = |\bar{Z}| \sin(\theta)$$

3. Use the results of steps 1 and 2 to solve for the $C_m$, $R_m$, and $R_b$, using Equations 9, 10, and 11, respectively.

In regard to values for muscle properties, they are derived from mice, but are essentially the same for human patients. It is the aortic banded mice which will be similar to the diseased and failing human hearts where AICD and bi-vent pacers are placed, and where placement of the epicardial admittance electrodes is targeted.

In normal myocardium, the relative permittivity of myocardium derived from measurements at 20 kHz was $\varepsilon_m = (11844 \pm 2700) \cdot e_0$ F/m, and the electrical conductivity of myocardium was measured at $\sigma_m = 0.160 \pm 0.046$ S/m. In banded hearts, $\varepsilon_m = (21267 \pm 8005) \cdot e_0$ F/m, a significant increase in myocardial properties ($11844 \pm 2700$ to $21267 \pm 8005) \cdot e_0$ F/m occurred compared to control ($p < 0.05$). The myocardial conductivity showed no significant change between banded $\sigma_m = 0.200 \pm 0.080$ S/m and control $\sigma_m = 0.160 \pm 0.046$ S/m (p=NS) hearts.

Figure 6:
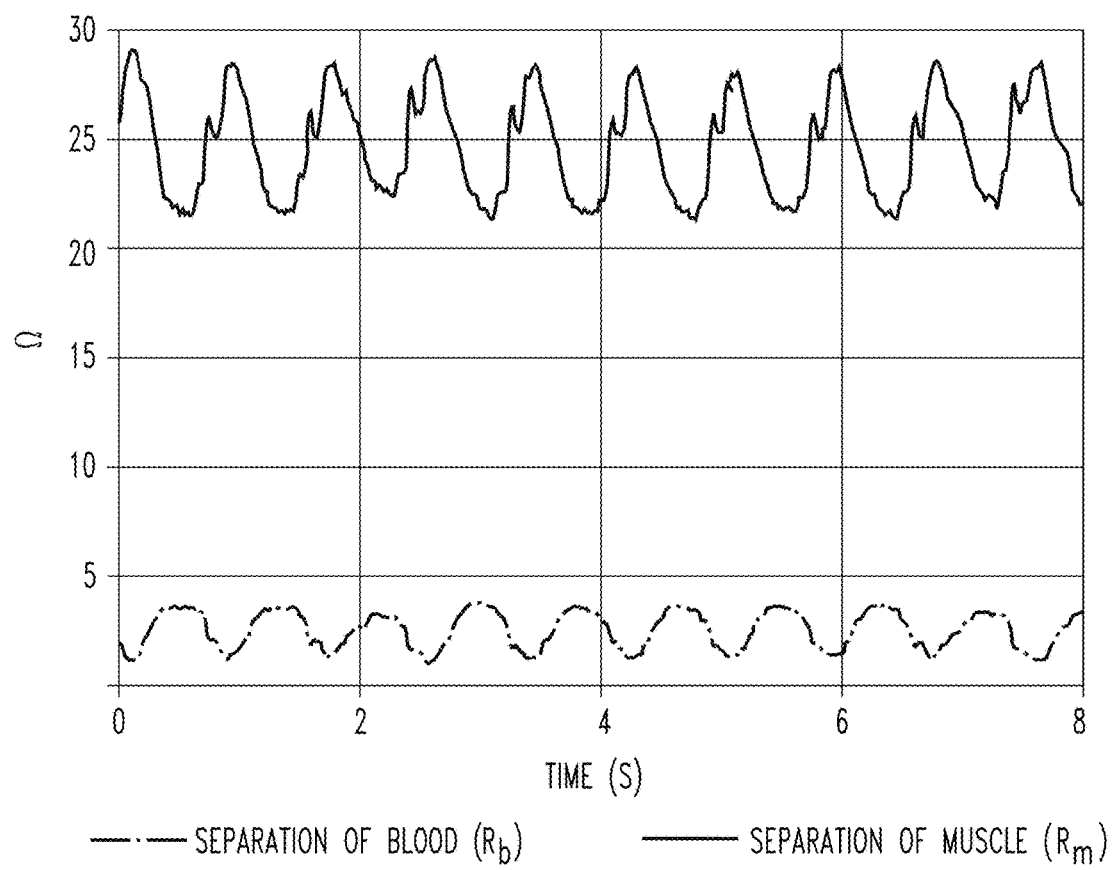
FIG. 6 shows separation of blood ($R_b$) and muscle ($R_m$) components from the combined signal.

As shown in FIG. 6, the blood and muscle components are able to be separated from the combined signal in real-time using the epicardial admittance approach.

FIG. 6 shows separation of blood ($R_b$) and muscle ($R_m$) components from the combined signal.

Successful derivation of real-time LV volume using the epicardial admittance approach. A real time LV volume signal has been successfully obtained with the Admittance approach described here. In this acute open chest porcine study, short axis admittance electrodes 16 were placed on the epicardium, and simultaneous ultrasonic crystals on the endocardium. Using the electrical model approach outlined above, a real time LV volume signal was successfully derived from both approaches, and overly them to demonstrate that the Epicardial Admittance and Endocardial ultrasonic crystals provide identical results (FIG. 7).

Figure 7:
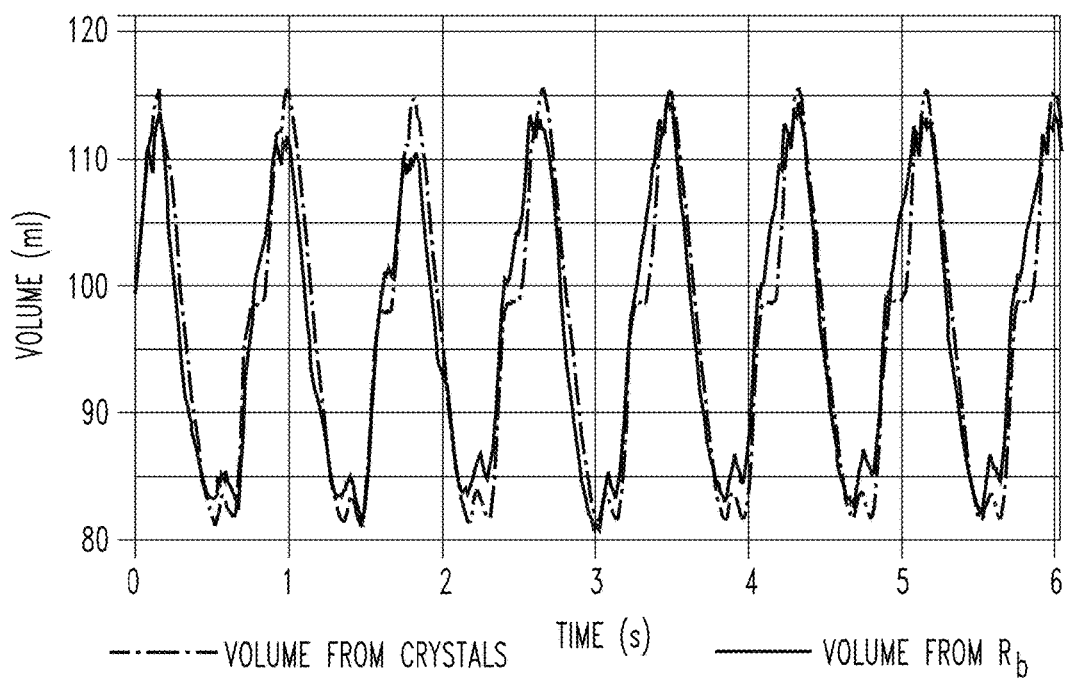
FIG. 7 shows simultaneous epicardial admittance derived LV volume (Rb) and endocardial ultrasonic crystals demonstrating that our proposed technique can provide an identical real-time volume signal as a standard.

FIG. 7 shows simultaneous epicardial admittance derived LV volume (Rb) and endocardial ultrasonic crystals demonstrating that our proposed technique can provide an identical real-time volume signal as a standard.

As can be seen in FIG. 7, the volumes derived from the echo crystals using Teicholtz's formula [see "The American Journal of Cardiology" Vol. 37, pages 7-11, January 1976] closely match the values derived using Baan's equation with a variable length between the voltage contacts (L).

Admittance derived distance as an alternative to absolute LV volume. We have demonstrated that impedance magnitude and phase are both highly correlated with distance as well, which implies that the LV dimension could be inferred by the measurement itself. The data below were acquired from an open chest porcine study with epicardial admittance electrodes 16 sewn onto the anterior and posterior myocardium. At the same time, an open chest 2D echocardiogram was obtained with an acoustic standoff (saline), and data from the admittance signal (Z) and echocardiogram (cm) were obtained simultaneously. As demonstrated in FIG. 8, both the epicardial admittance derived real time dimension (Z) and short axis 2D echo distance are super imposable, consistent with admittance derived dimension being an alternative endpoint besides absolute LV volume.

Figure 8:
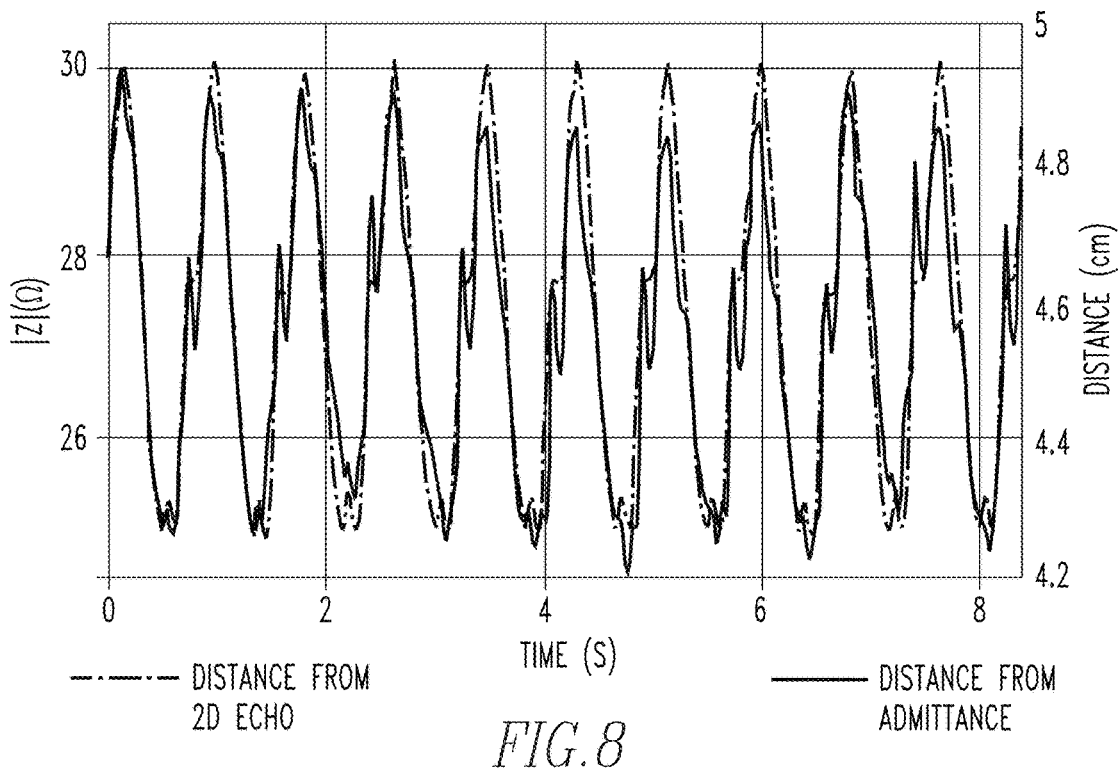
FIG. 8 shows that the LV epicardial admittance technique can also provide the identical real-time LV dimension or distance as short axis 2D echocardiography. LV distance from admittance will provide an alternative use of epicardial admittance to warn of impending heart failure.

FIG. 8 shows that the LV epicardial admittance technique can also provide the identical real-time LV dimension or distance as short axis 2D echocardiography. LV distance from admittance will provide an alternative use of epicardial admittance to warn of impending heart failure.

Figure 9B:
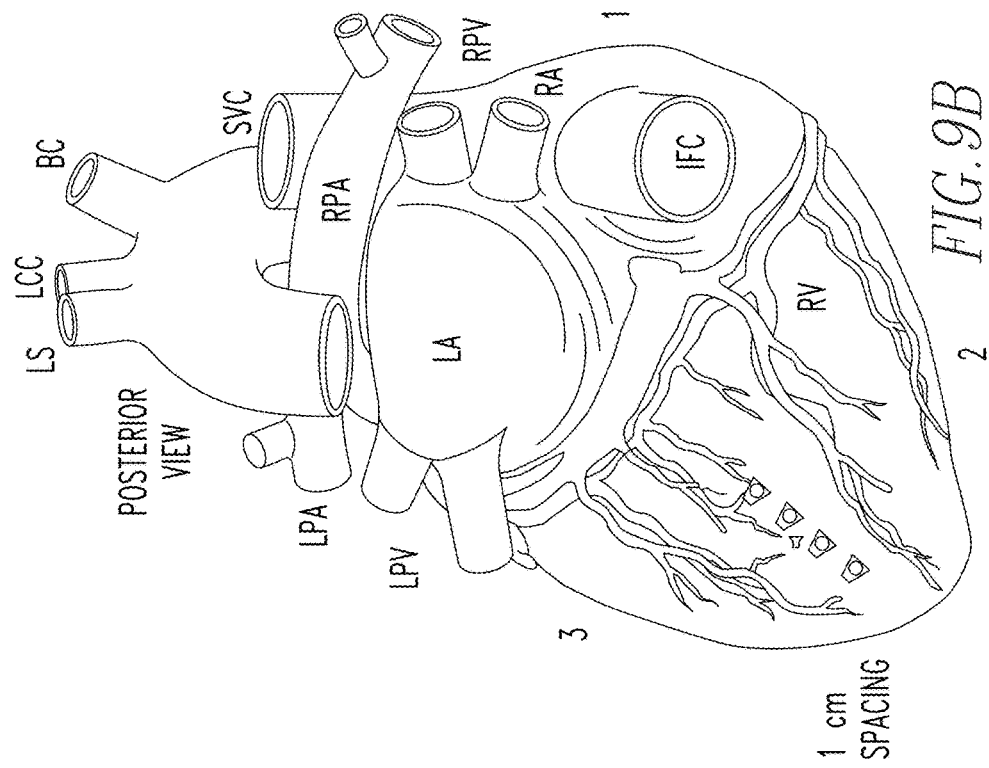
FIGS. 9a and 9b show endocardial Sonomicrometry Crystals and Epicardial Admittance Electrode Placement. Stimulation is across the LV chamber, from anterior to posterior.
Figure 9A:
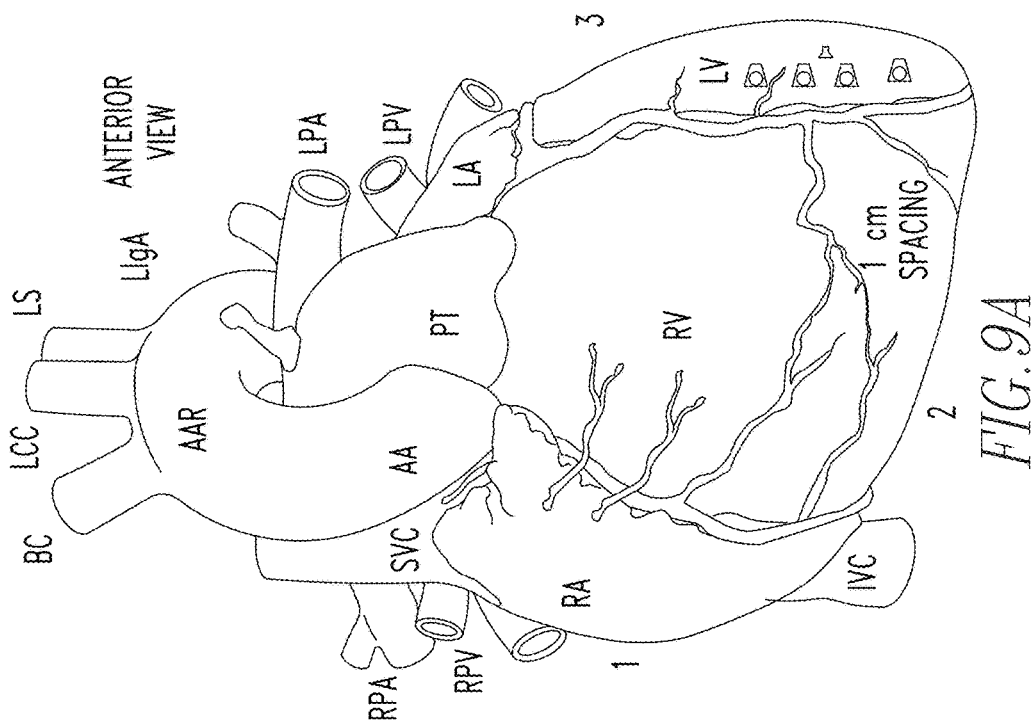

The placement of the epicardial admittance electrodes 16 and the endocardial sonomicrometry crystals is shown in FIGS. 9a and 9b. The preparation is an open chest porcine model. There are four pairs of admittance electrodes 16 shown by the trapezoids, and of each electrode in the pair, one is current stimulating, and the other is voltage sensing (only two pair shown in FIG. 9a). In this way, an admittance measurement is made which stimulates across the chamber from the anterior to the posterior side of the LV. The endocardial sonomicrometry crystals are placed as shown on the diagram in FIG. 9b as well, and serve as a standard for LV volume. Long axis crystals were also placed and are not shown in this figure.

FIGS. 9a and 9b show endocardial Sonomicrometry Crystals and Epicardial Admittance Electrode Placement. Stimulation is across the LV chamber, from anterior to posterior.

Pig 1 dynamic signals are shown and affected by breathing artifact because the respirator was not turned off. This was designed to demonstrate the effect of breathing on the measurement. As is visibly evident in FIG. 10, the fiduciary points of the length tracing from the short axis crystals are 180 degrees out of phase with the blood resistance signal.

Figure 10:
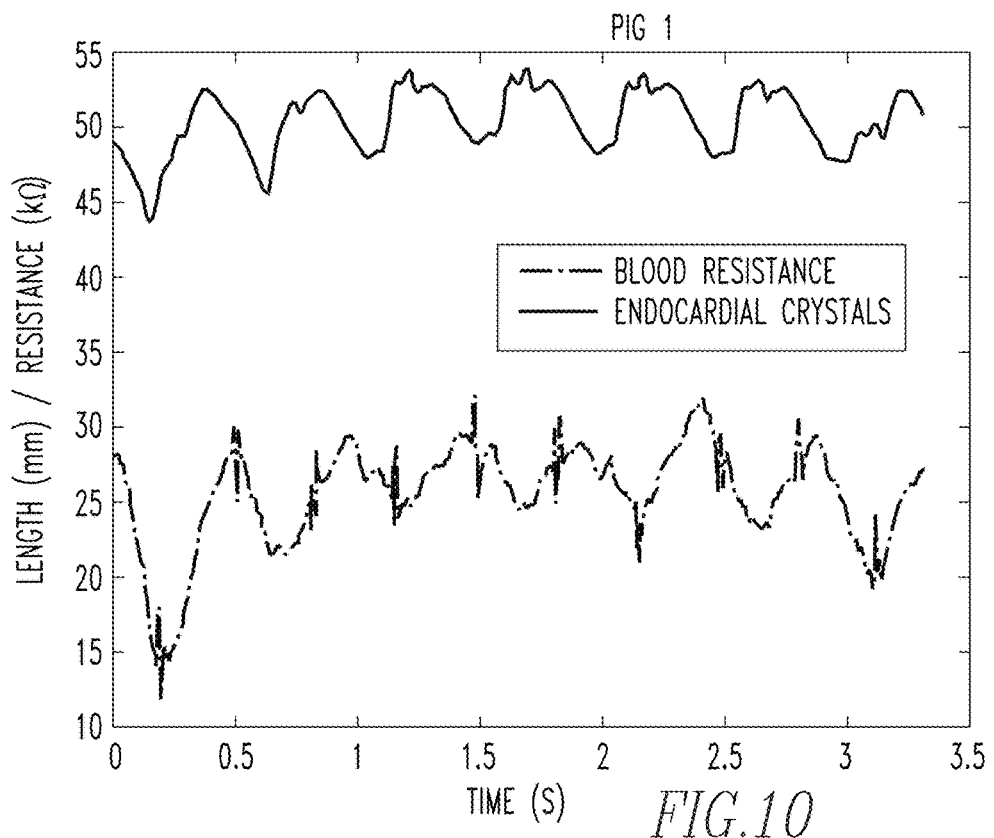
FIG. 10 shows real-time steady state data from Pig 1 demonstrating the blood resistance extracted from the combined myocardium/blood voltage signal generated as measured with the Epicardial Admittance Electrodes, and the Endocardial Sonomicrometry Crystals data for comparison.

FIG. 10 shows real-time steady state data from Pig 1 demonstrating the blood resistance extracted from the combined myocardium/blood voltage signal generated as measured with the Epicardial Admittance Electrodes 16, and the Endocardial Sonomicrometry Crystals data for comparison.

The same measurements are also displayed from Pig #2 with the respirator turned off for the measurements. Similar electrode positioning was used, and again the blood resistance and crystals signals are 180 degrees out of phase.

Figure 11:
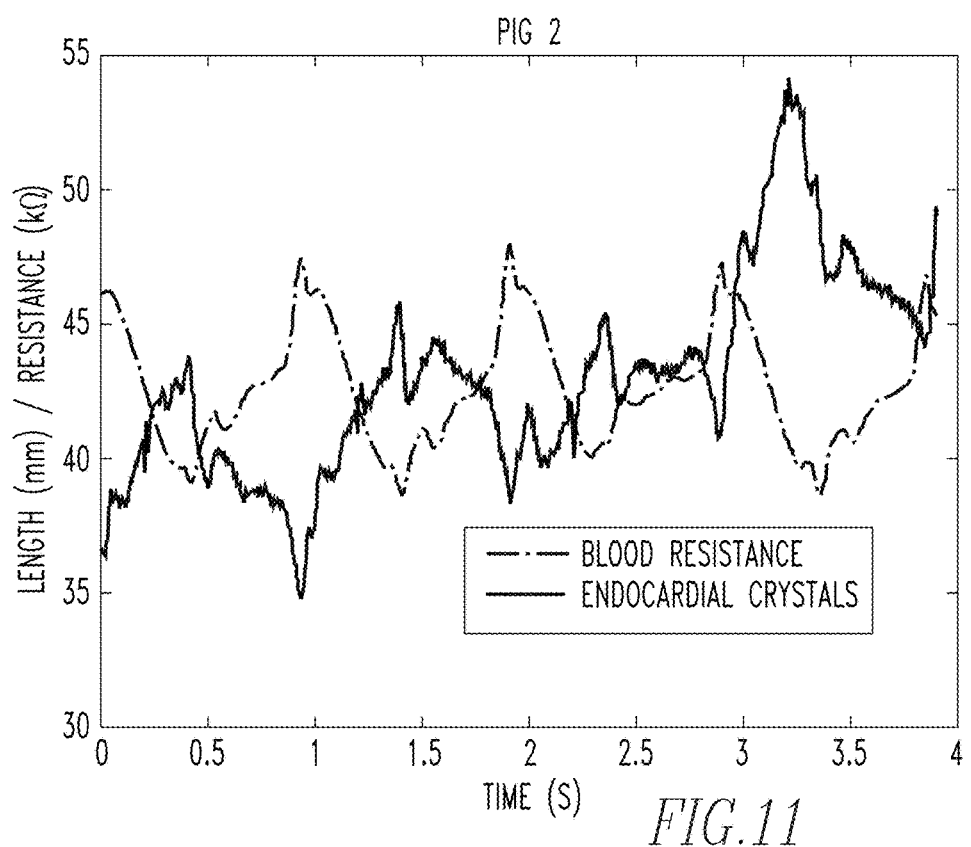
FIG. 11 shows steady state data for Pig 2.

FIG. 11 shows steady state data for Pig 2.

As the LV longitudinal axis cross section area increases, there is a fall in blood resistance due to the increase in the cross sectional area of blood (a high conductivity tissue). Baan's equation converts resistance to volume by assuming a constant L, while here, the epicardial admittance electrodes move with the heart and have a dynamic L. The endocardial crystal distance L is directly related to the measured blood resistance, and in current experiments seem to determine the offset of the signal.

Application of Increased Load with IV Neosynephrine Infusion to Simulate LV Dilation.

The short and long axes crystal distances are both increasing as the Neosynephrine dose is increased. All of these signals are taken over a single respiratory cycle, a duration of approximately 3.5 seconds, thus the "drift" is due to breathing artifact. These results are consistent with experimental preparation successfully dilating the LV similar to how a patient left ventricle would dilate prior to the onset of heart failure.

Figure 12:
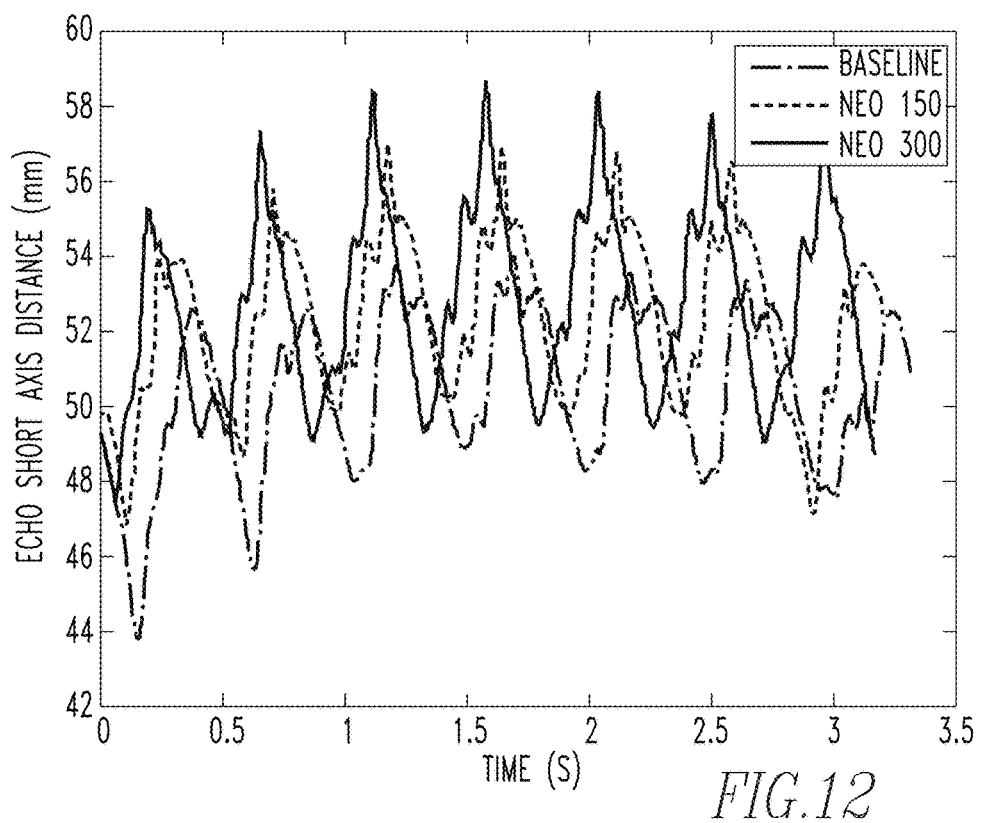
FIG. 12 shows Short Axis endocardial crystal data during Baseline, 150 µg/min Neosynephrine, and 300 µg/min Neosynephrine steady state IV infusion demonstrating that we can achieve steady state LV dilation with our surgical preparation.

FIG. 12 shows Short Axis endocardial crystal data during Baseline, 150 μg/min Neosynephrine, and 300 μg/min Neosynephrine steady state IV infusion demonstrating that we can achieve steady state LV dilation with our surgical preparation.

Figure 13:
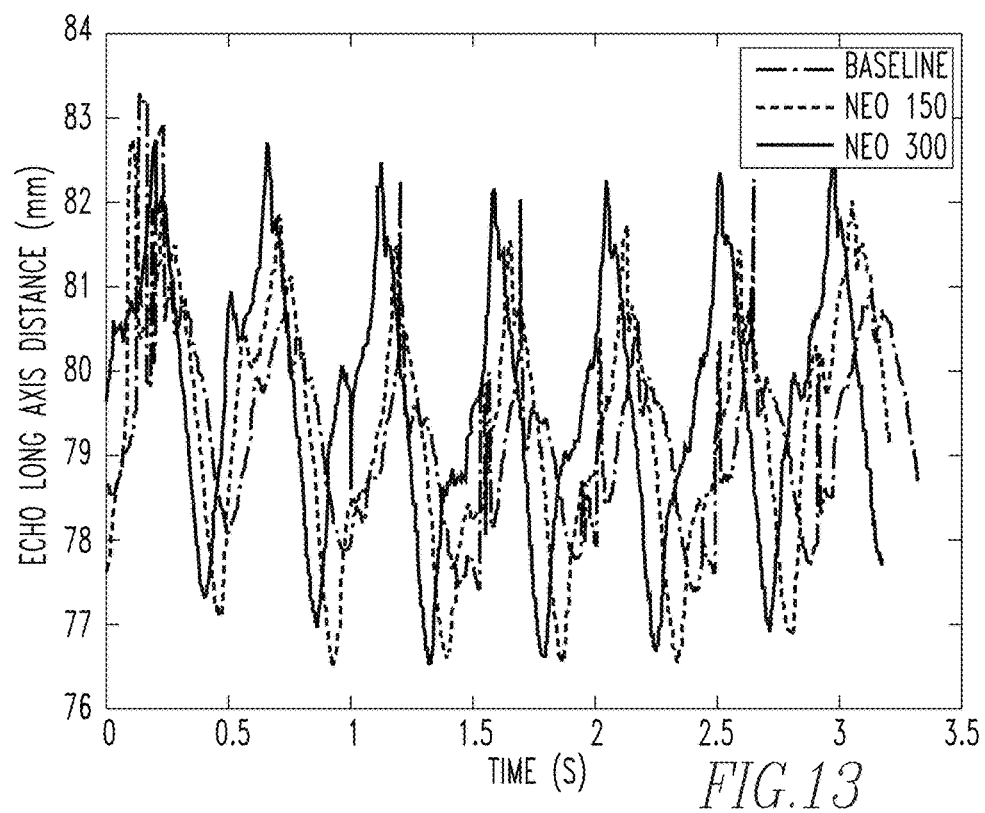
FIG. 13 shows long axis crystal data during Baseline, 150 µg/min Neosynephrine, and 300 µg/min Neosynephrine steady state IV infusion.

FIG. 13 shows long axis crystal data during Baseline, 150 μg/min Neosynephrine, and 300 μg/min Neosynephrine steady state IV infusion.

Figure 14:
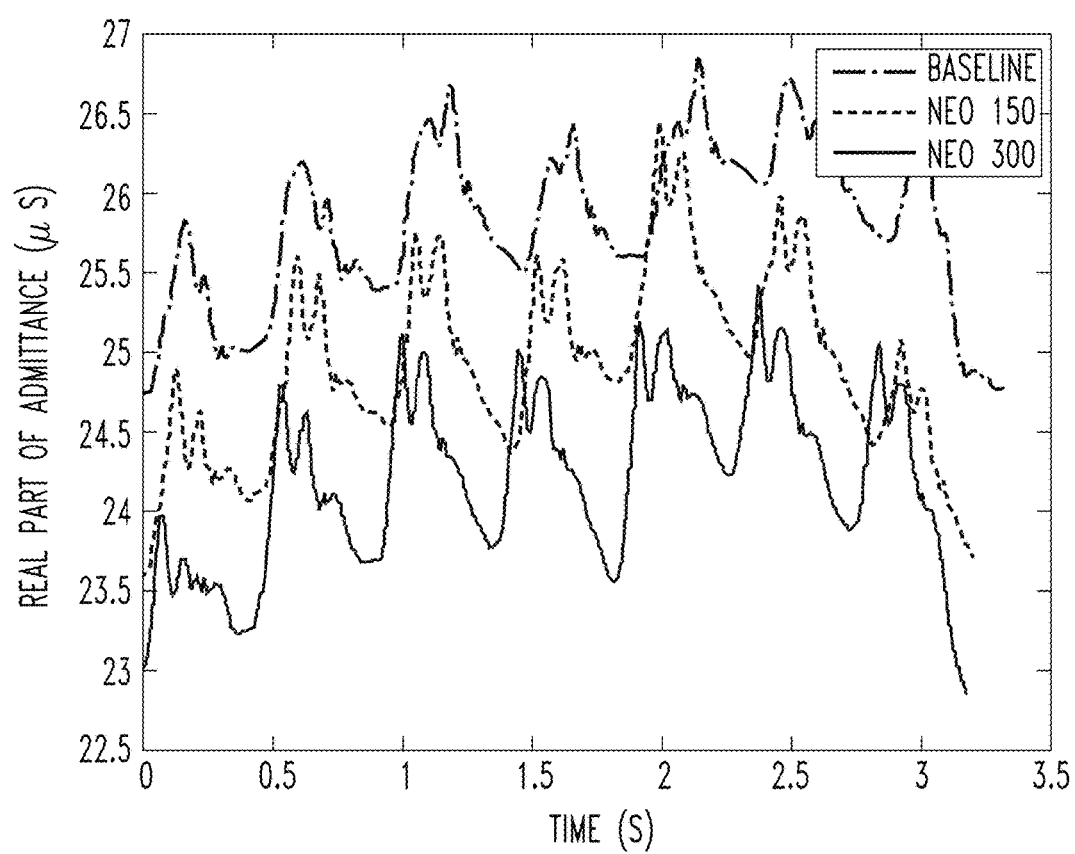
FIG. 14 shows the real part of the Admittance signal demonstrates that the measurement is sensitive to steady state loading changes.

As shown in FIG. 14 from pig #1, the real part of admittance signal changes as the LV dilates with Neosynephrine infusion. Breathing drift is also seen in the admittance data.

FIG. 14 shows the real part of the Admittance signal demonstrates that the measurement is sensitive to steady state loading changes.

FIG. 14 shows that because as the epicardial electrodes 16 move further apart (as with impending heart failure), the resistance between the electrodes 16 increases (implying a decrease in conductance). Keep in mind that these signals were obtained with the respirator on to simulate breathing artifact.

Figure 15:
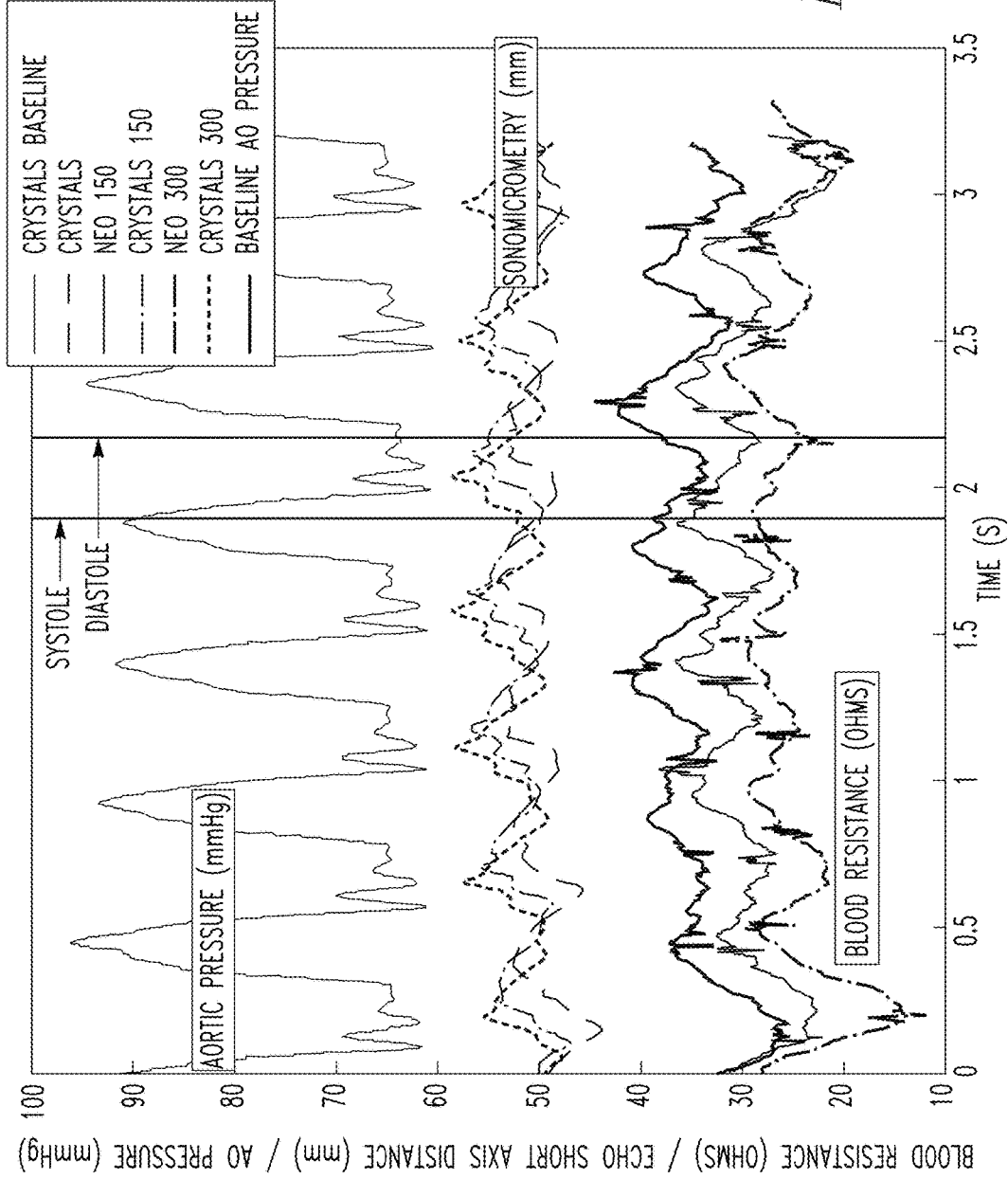
FIG. 15 shows all signals for Baseline, 150 µg/min Neosynephrine, and 300 µg/min Neosynephrine steady state IV infusion with increased afterload and subsequent LV dilation successful detected with epicardial admittance for Pig 1.

FIG. 15 shows all signals for Baseline, 150 μg/min Neosynephrine, and 300 μg/min Neosynephrine steady state IV infusion with increased afterload and subsequent LV dilation successful detected with epicardial admittance for Pig 1.

Figure 16:
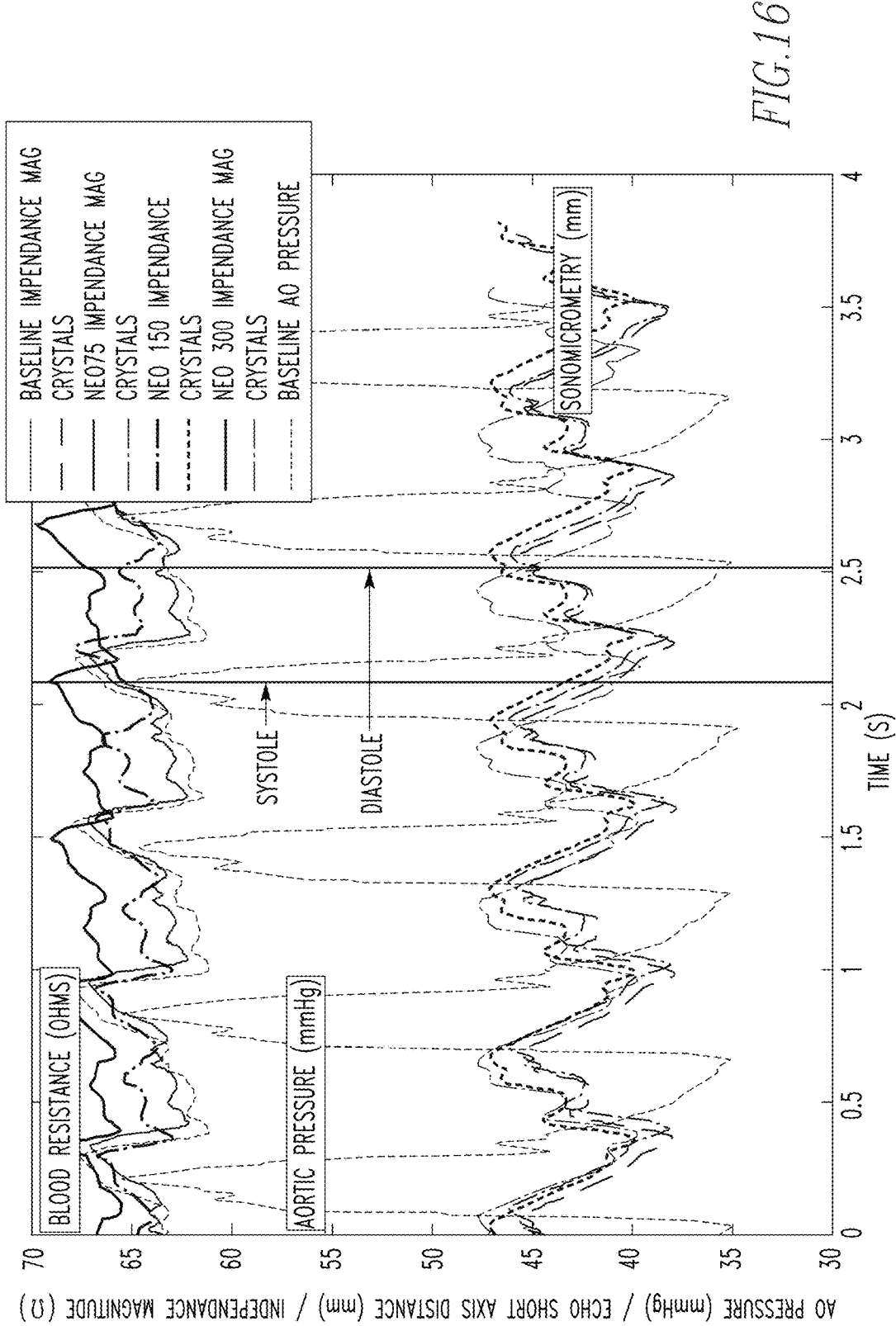
FIG. 16 shows all signals for Baseline (red), 150 µg/min Neosynephrine, and 300 µg/min Neosynephrine steady state IV infusion with increased afterload and subsequent LV dilation successful detected with epicardial admittance for Pig 3.

FIG. 16 shows all signals for Baseline (red), 150 μg/min Neosynephrine, and 300 μg/min Neosynephrine steady state IV infusion with increased afterload and subsequent LV dilation successful detected with epicardial admittance for Pig 3.

Figure 17:
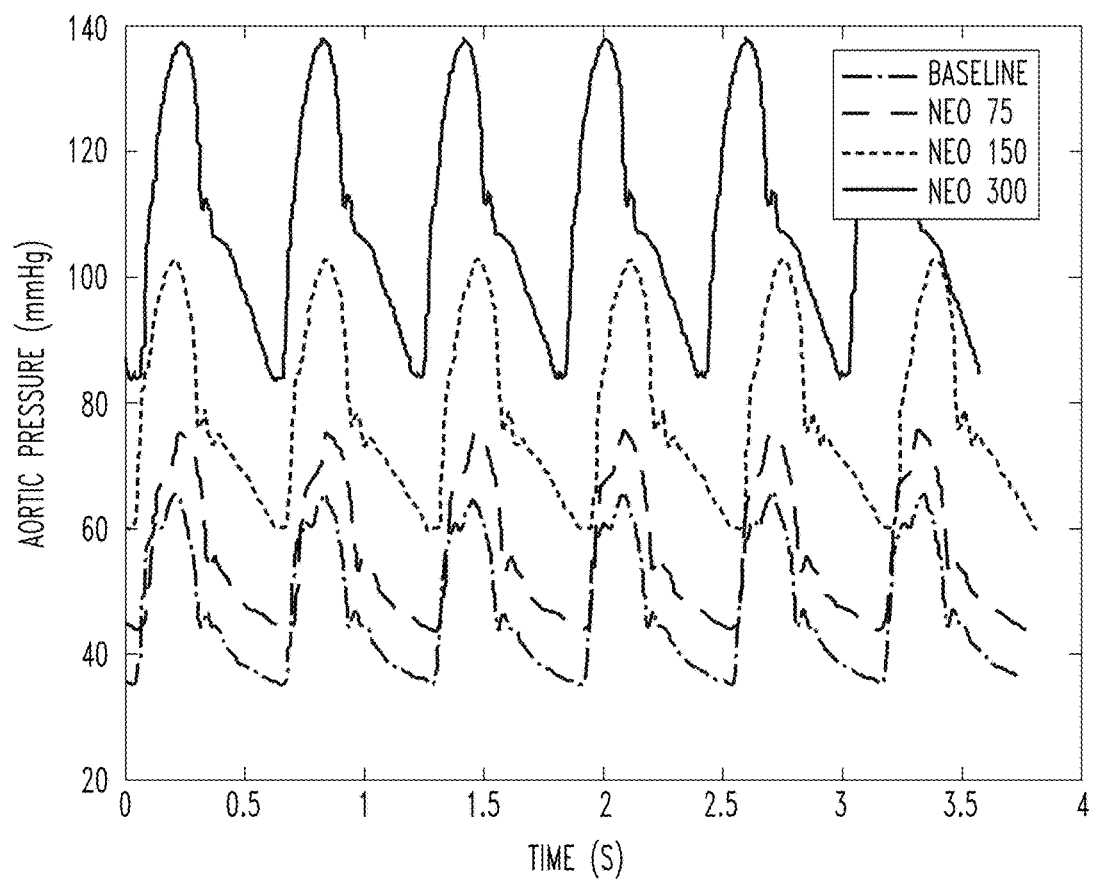
FIG. 17 shows aortic pressure changes during Neosynephrine infusion.

FIG. 17 shows aortic pressure changes during Neosynephrine infusion.

Figure 18:
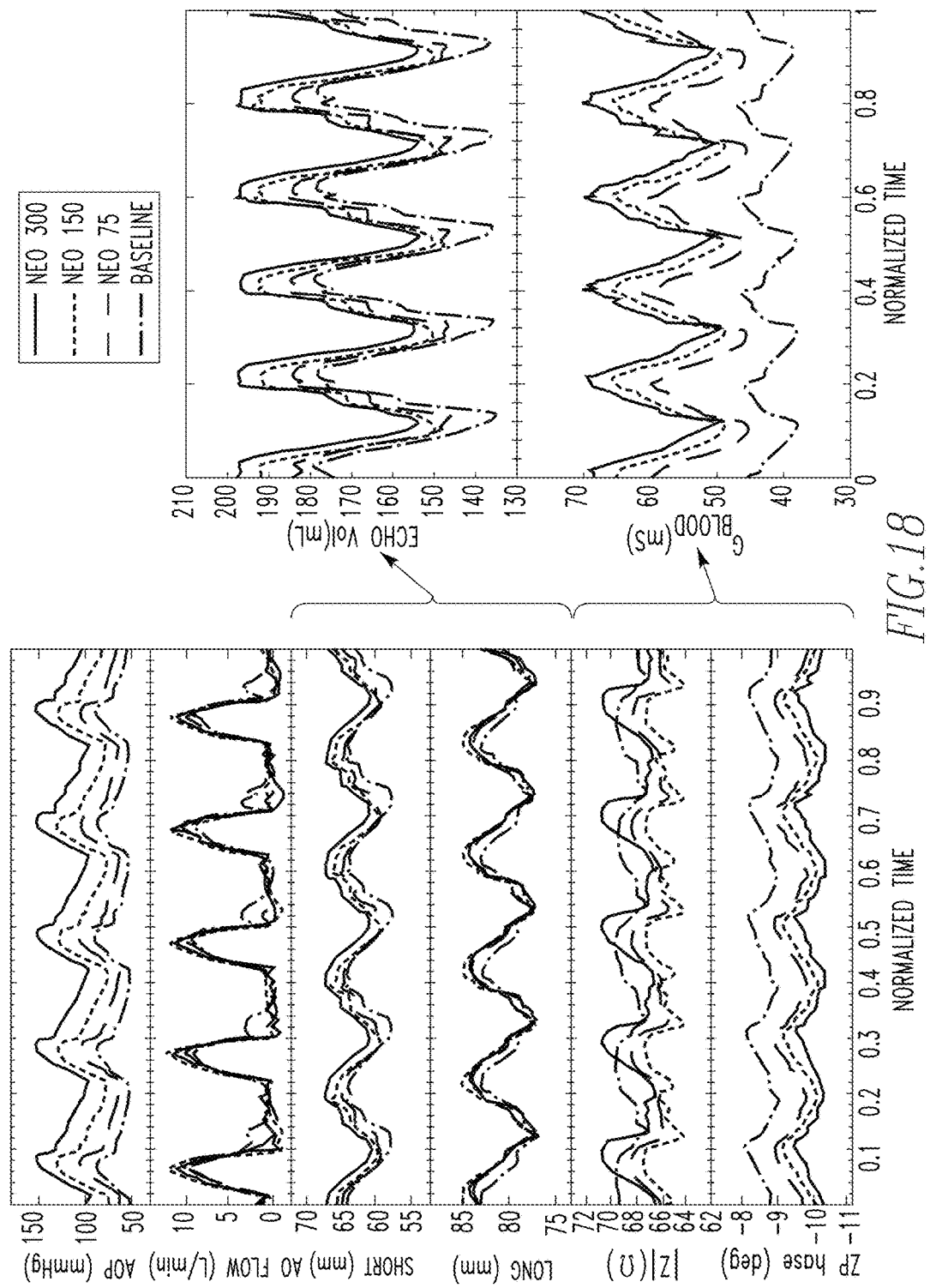
FIG. 18 shows that both the echo crystal derived volume and blood conductance (Gb) signals derived from the LV both increase in response to increasing loading conditions in response to IV Neosynephrine infusion, which simulates LV dilation as would occur in patients with congestive heart failure.

FIG. 18 shows that both the echo crystal derived volume and blood conductance (Gb) signals derived from the LV both increase in response to increasing loading conditions in response to IV Neosynephrine infusion, which simulates LV dilation as would occur in patients with congestive heart failure. In addition to the end-diastolic volume in milliliters (mL), or end-diastolic blood conductance in mS (milliSiemens), as a measure of impending heart failure, the end-systolic volume or end-systolic blood conductance are also of great interest as a physiologic measure of the heart in general, and specifically, LV contractility (measure of muscle strength). The minimal size that the heart can accomplish is a well accepted measure of muscle strength, where the smaller the size obtained, the stronger the heart, and the larger the minimal size of the heart, the worse the muscle strength or contractility [see Cardiology textbook entitled—Braunwald's Heart Disease: A Textbook of Cardiovascular Medicine, $7^{th}$ edition, volume 1, page 495]. Thus, the end-systolic blood conductance derived with the admittance system will be used as measure of LV contractility, whereas the end-systolic blood conductance increases, the physician and patient will have knowledge of a weaker heart, and as the LV end-systolic blood conductance decreases, evidence of a stronger heart will be evident.

Figure 19:
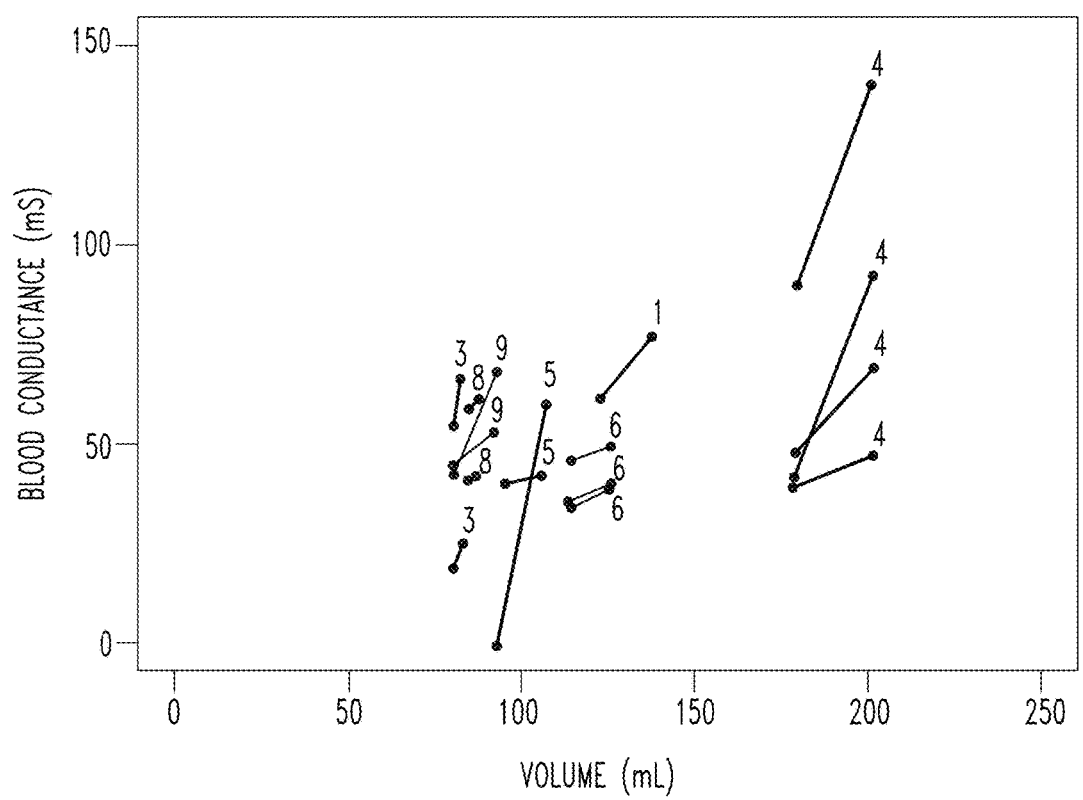
FIG. 19 is a graph that demonstrates the increased sensitivity of the admittance system compared to ultrasonic echo derived blood volume to an increase in LV blood volume in response to Neosynephrine infusion.

FIG. 19 demonstrates the increased sensitivity of the admittance system compared to ultrasonic echo derived blood volume to an increase in LV blood volume in response to Neosynephrine infusion. Data included in this figure was derived from n=7 porcine open chest experiments, with n=16 area dependent vectors (the details of the experiment preparation have been described elsewhere in this application). Individual animals are identified by different symbols, with some pigs having only a single vector, and others having 3 or 4 vectors displayed. The overall average of the within-animal slopes was 1.6 mS/mL (milliSiemens/milliliters), with a standard deviation of 1.1 mS/mL. Based on a one-sample t-test this average slope is significantly different from zero (p=0.01), implying that the admittance approach can detect an increase in LV volume from heart dilation. Thus, the admittance approach has at least 1.2 times and preferably 1.6 times the sensitivity to detect an increase in LV dilation than the standard.

In regard to calibration, there are many possible sources of error in a measurement of admittance, including offset or gain error which is brought on by the measurement system itself and error from the electrode-electrolyte interface effects as described below. These sources of error must be accounted for in order to make an accurate measurement.

For admittance instrument calibration, a 5 segment multiple gain conductance measurement system called a GX5 (Scisense, London, ON) was retrofitted with a 5 segment phase measurement system to create a 5 channel admittance measurement system. In order to ensure proper functionality, the input of this system was attached to a potentiometer and capacitor and the total impedance was varied over the range of the real and imaginary planes of measurement. These were then checked against the theoretical admittance which would be produced by each RC load, to make sure that no significant error was introduced by the system itself. In the GX5 system, the error introduced by the system is minimal. It is important to note here that there is a significant difference between the complex (non-real) measurement of "admittance", and the more common measure of "conductance". Any measurement of admittance (or impedance, its inverse) requires measurement of both magnitude and phase angle. Previous technology using conductance for the detection of blood pool size is problematic because it cannot quantify the amount of conductance coming from parallel structures such as muscle. Admittance solves this problem through the use of a phase measurement which allows determination of the amount of cardiac muscle signal present in the measurement. It is because of this fact that phase measurement is fundamentally a part of complex admittance or impedance measurement.

For LV epicardial lead calibration, there is no magnitude or phase offset present in the measurement because of the box. At the point where the admittance instrument calibration is complete, it has been essentially calibrated out to the plane of the input terminals to the GX5. However, there is still the effect of the electrodes 16 and electrode/electrolyte interface to consider. Because the assumption of the impedance separation equations (Equations 30 and 31) is that the electrode capacitance is negligible, this assumption should be tested before each experiment. In order to check this assumption, the electrodes 16 are submerged in saline of conductivity σ=8000 μS/cm and the output of the GX5 is checked for a phase angle shift (indicating measurable capacitance from the electrodes 16 or the electrode/electrolyte interface effect). The conductivity of pig blood averages to around this value of conductivity, and saline is used because it does not introduce a phase shift in an impedance measurement ($\in_r \approx 80$, roughly the same as water). Because all complex impedance in this system must be capacitive, (an inductive load could cancel out this result) and because the electrodes 16 never produce more than 1 degree of phase shift on the output, regardless of orientation, they do not require calibration beyond this point in the study. All measured phase shift should be due to the physiologic system being measured.

For surface probe calibration, the biggest difference between a pig probe and the previously described mouse probe is of course the size. The length between the current stimulating electrodes 16 on the surface probe determines the penetration depth of the measurement field, and this electrode is designed for a larger penetration depth because the pig LV myocardium is roughly 10 mm thick. This larger spacing also reduces the amount of interwire capacitance in the probe, which increases the standard deviation of muscle properties in a mouse measurement.

The surface probe is calibrated exactly as the surface probe is calibrated in "Electrical Conductivity and Permittivity of Murine Myocardium" by K. Raghavan; IEEE Transactions on Biomedical Engineering, Vol. 56, No. 8 (August 2009), incorporated by reference herein. Saline solutions of conductivity σ=2000, 4000, 6000, 8000, and 10000 μS/cm span the range of conductivities necessary to measure myocardial properties, and the phase offset due to the surface probe is recorded after measurement of the surface of these 5 solutions. This phase offset is then removed from the measurement itself by subtracting the probe's contribution to the susceptance.

In regard to surgical preparation, the open chest surgical preparation for a pig is a complicated mix of anti-arrhythmic agents (for hemodynamic stability) and alpha agonists (for increased blood pressure). It is often quite difficult to find the right proportion of stability and signal degradation which will give acceptable results and keep the subject alive for the duration of the experiment. In this experiment, the following protocol was used:

1. Pig is given Tealazol (0.5 ml) via intramuscular injection and transferred to the operating suite.
2. Isoflurane is given to induce an appropriate plane of anesthesia.
3. After the right carotid artery is cannulated and a pressure sensor is introduced for Aortic Pressure to monitor the pig's condition, a 150 mg infusion of Amiodarone (an anti-arrhythmic) is given to prevent fibrillation upon opening the chest.
4. The chest is opened via sternotomy, and we allow 30 minutes pass to ensure that the pig has time to recover from the initial Amiodarone infusion, and before the next Amiodarone infusion.
5. A second 150 mg infusion of Amiodarone is given. At this point, the pigs hemodynamics are depressed because Amiodarone and/or its solvent are negative inotropes.
6. If the blood pressure ever dips below about 70 mmHg systolic, a 1 mg bolus of Atropine is given to raise pressures. Normal systolic blood pressure in mammalian hearts is usually above 100 mmHg, but under anesthesia, a much lower number can be expected.
7. After the last bolus of Amiodarone is given in step [00147], the pig is put on IV Lidocaine drip 1 mg/min for the remainder of the experiment. The Lidocaine acts as an analgesic without depressing the hemodynamic system.
8. Additionally, Lidocaine is used as a topical analgesic to prevent pain response when sewing an electrode patch or sonomicrometry crystal directly to the myocardium.
9. At this point, the rest of the instrumentation is added to the preparation. If, during the experiment, the additional Atropine and Lidocaine is not enough to increase pressures to a point which ensures survivability within about 5-10 minutes of the dose, Neosynephrine is given at 10-25 μg/min (an alpha angonist).

For myocardial properties protocol, myocardial conductivity and permittivity are measured using the surface probe whose calibration was outlined above. The pig anatomy is large enough with respect to the probe size to find an area of the muscle which is devoid of blood vessels. This is usually an area near the placement of the anterior electrodes 16, but lateral to the Left Anterior Descending Coronary Artery. N=3 measurements are taken in two positions which are perpendicular to each other over a large patch of myocardium (not over a coronary blood vessel), to ensure that myocardial properties do not change with probe orientation. These measurements are retaken throughout the protocol because an extended period of surgery can cause noticeable changes in health and hydration of the myocardium, and these measurements are retaken to ensure that our signals can be accurately recalibrated at any time during the preparation.

The epicardial lead measurement protocol requires instrumentation in the following locations sewn onto the myocardial surface itself. In practice, it was found to be easier to sew the admittance electrodes 16 to a felt backing, and then suture the felt backing to the myocardial surface, to prevent arrhythmia due to trauma on the surface of the heart from multiple stitches. The locations of all myocardial surface instrumentation are shown in FIGS. 9a and 9b. The epicardial impedance electrodes 16 are spaced 1 cm apart each because this is a common spacing for intraventricular catheters, and also allows for simulation of surgical error when placing the electrodes 16.

There are 4 epicardial impedance electrodes 16 sewn to the anterior surface of the heart, and 4 sewn to the posterior surface as shown in FIGS. 9a and 9b. When taking measurements, two from the anterior surface are chosen and two from the posterior surface are chosen to perform a tetrapolar measurement. Each group of 4 possible electrodes (without reflection) is referred to as a "vector" for the rest of this discussion. There are 9 vectors total, each one representing a separate measurement of impedance across the LV. In an open chest experiment, the heart straddles the lungs, and the lungs are expanding and recoiling with each breath. Motion artifact is created by the lungs which is evident in both the impedance measurement and the sonomicrometry measurements. To eliminate this source of artifact, the respirator was turned off for about 5 seconds for each vector. Time was given to let the pig recover between measurements. In the current preparation, the electrodes 16 are connected to an impedance measurement system which is manufactured by Scisense Inc, London, Canada (using wires). In general, this measurement could be attached to an impedance measurement system which is implanted (using implantable wires).

Regarding the Neosynephrine protocol, neosynephrine is an alpha agonist that increases afterload and secondarily dilates the LV. Neosynephrine increases the afterload that the heart pumps against only during the time it is being infused, and it takes approximately 20 minutes in the pigs for the effect of Neosynephrine to wear off. Neosyneprine is also given at a lower dose (10-25 µg/min) if necessary to maintain physiologic pressures for survivability early in the surgical preparation, so this dosage is stopped 20 minutes before the first baseline is acquired. At baseline, the following are measured: aortic flow, aortic pressure, right ventricular pressure, impedance magnitude and phase for each vector, and both apex/base and anterior/posterior sets of sonomicrometry for verification of volume.

In this experiment, after baseline data is taken Neosynephrine is given at a rate of 37.5, 75, 150, and 300 µg/min for 10 minutes each to induce a steady state of volume and pressure increase. Then impedance magnitude and phase are recorded along all 9 vectors across the LV. The theory behind a traditional conductance measurement explains that as the LV chamber fills with blood, the total blood resistance decreases due to the increase in cross-sectional area of blood (because of the increased blood volume). This same phenomenon should be present in the measurement of blood volume when using epicardial electrodes as well. However, there is also a variable distance between the stimulating and sensing electrodes in the impedance measurement suggested above, which will affect the signal inversely. Therefore, as the length increases between the apical and lateral electrodes, the resistance of the blood should increase, but as more blood fills the ventricle, the cross-sectional area will increase, making more parallel pathways for current which causes the resistance to decrease. It is possible that because the length and the area are related, the resistance measured could be nullified by these two effects. However, it is also quite possible that because both change as the heart beats, the effect of the change in cross-sectional area could be minimized by looking at the points where the heart is largest (at end diastole).

It is because of the above reasons that all that is necessary is the detection of a change in baseline blood conductance (or its inverse, resistance) to determine whether heart failure is ongoing in a patient.

Transient aortic occlusions were performed to supplement the Neosynephrine steady state protocol because it is a "purer" method of LV volume increase. To create such an LV volume loading change, a water filled balloon occluder is sutured around the descending thoracic aorta and inflated slowly until the Ao pressure reaches approximately 150% of its baseline value. This briefly causes the LV volume to increase, and at the same time, measurements are taken as in the previous protocol. Using this technique, it has been demonstrated that as the LV dilates without the use of pharmacologic manipulation, the derived blood resistance from the admittance technique will decrease, and its inverse, blood conductance will increase.

A possible source of artifact for impedance measurement in heart failure patients comes from the accumulation of pleural effusions. At the end of the epicardial lead experiment, a pleural effusion is simulated by filling the space between the heart/pericardium and lungs with using saline of conductivity $\sigma=8000$ µS/cm to determine if fluid in this space will be a source of artifact for the admittance approach.

Before the pleural effusion procedure, any extra liquid in the pleural space (usually blood) is suctioned out, and a baseline measurement is taken across every vector. Enough saline to cover the posterior electrodes 16 and most of the heart is introduced into the pleural space. This is approximately 300-350 mL depending on the size of the pig. Care is also taken to make sure that the heart is not buoyant on the saline to prevent an unnatural re-positioning of the heart. Measurements of the impedance across every vector are performed after the saline is introduced, and the results are recorded. It has been demonstrated there is no change in measurements due to the artifact of a simulated pleural effusion.

The placement for electrodes 16 in other organs is organ specific. Since the left ventricle is physiologically the chamber most likely to dilate before the onset of heart failure, it is easier to focus on placing the electrodes 16 in areas which span the left ventricle. However, in other organs it is important to place the electrodes 16 such that the path of the stimulating field crosses the area which will change conductivity and permittivity. For example, if trying to detect ischemia, one would place the electrodes 16 on the surface of the area of interest, and look for permittivity decrease. If looking for good kidney function one would look for a conductivity decrease due to the lack of fluid in the kidneys, etc. This can easily be extended into humans by placing the admittance circuitry in the stimulation pack which is implanted as part of all AICD/Biventricular pacemakers. Only a few extra electrodes 16 need to be added to make a robust measurement, and the placement of the electrodes 16 will be the two RV electrodes 16 (ring and tip which already exist), and two electrodes 16 in the coronary sinus with extension into a lateral epicardial coronary vein (which will need to be added). These two electrodes 16 in the lateral epicardial coronary vein are on a catheter extending from the AICD. A drive circuit, such as the one described below is added to the AICD/Biventricular Pacemaker and connected to the electrodes 16 to generate the signal. In order to implement telemetry, an already existing microcontroller from TI called the ez430 (a subset of the MSP430 package is used). This microcontroller samples the analog signals it receives from the electrodes 16 and sends them to a remote computer wirelessly using XBEE protocol. The admittance analysis is performed at the remote computer. Telemetry does already exist in current pacemaker and AICD technology, but its range is only a few inches. The XBEE device (ez430) is used instead because it has a much larger range (and can therefore be integrated with a computer which is hooked up to a router for signaling physicians). It should be noted that the echo crystals are only used for validation in experiments in vivo. They are not intended to be implanted in actual use of the device.

As the state of congestive heart failure worsens, the volume of the LV chamber will increase, causing a detectable signal in the admittance system which is implanted. Afterward, telemetry, that is already part of the AICD/Bi-V pacemaker, will send a signal from the pacemaker to a receiver (in a hospital) or a router (in a home), which will alert the doctor that the patient needs to be brought in for further examination. The same information can be shared with the patient as well to alert the patient of impending heart failure, and encourage that patient to contact their physician.

The ideal physical location of the stimulating and sensing tetrapolar electrode pairs that will maximize the admittance signal to detect with greatest sensitivity a change in blood volume would be determined by trial and error by the electrophysiologist at the time of placement of the AICD-biventricular pacemaker. The rationale for this approach is that blood resistance is directly related to the length of the vector, and inversely related to the area of the vector. We have demonstrated that some vectors will be positively moving with LV dilation, and others negatively moving with LV dilation. These directional differences are determined by whether the vector is predominantly length or area dependent. As long as the operator at the time of implantation of the ACID-biventricular pacemaker is cognizant of whether the final vector chosen for a patient is area or length dependent, then LV dilation may be recognized by either an increase or decrease of blood resistance with LV dilation proceeding heart failure in that given patient. The most important decision made by the electrophysiologist at the time of implantation is whether the vector is maximally sensitive to a change in LV size, and not whether the vector is positively or negatively going. This can be tested at the time of implantation of the ACID-biventricular pacemaker by infusing drugs known to be safely used in heart failure patients, such as Nitroprusside, which will decrease LV volume in a dose-response fashion.

Additional applications for using admittance are described as follows. They use the same principles and technique described above but with modification, as described below, for the specific application.

1) Skin Burn Patients—A four electrode device on a planar surface is applied to the skin to differentiate dermis from epidermis during blister formation.

2) CNS—electrodes 16 are implanted in the brain at the time of neurosurgery and used in a post-surgical ICU setting to monitor for increased swelling of the brain, and increased cerebral spinal fluid in the ventricles.

3) Pulmonary Edema—Four electrodes 16 are implanted spanning across the lungs but on the chest surface to monitor for the development of pulmonary edema as a sign of congestive heart failure. These electrodes 16 could be placed on the anterior chest and back, for instance. In an alternative arrangement, these electrodes could be implanted between a heart lead, and the AICD-biventricular circuitry implanted as a pouch in the left and/or right upper chest of the patient, and the interrogated circuit span between the heart electrode and the circuitry. This is similar to the approach currently used by the Optivol® system developed by Medtronic Corporation; however, Optivol® does not use admittance, and does not correct for the motion of the heart lead with heart contraction and relaxation, but rather assumes a constant length between stimulation and sensing electrodes (L), which is a source of error for Optivol®.

4) Paraplegic patients would have n=4 skin electrodes 16 applied to the lower anterior abdomen (skin surface) to monitor when the bladder (placed over the bladder on the skin surface) is full so patients can self cath themselves to empty the bladder since they have no sensation of a full bladder.

5) Skeletal muscle edema from trauma—similar to burn patients (#1 above), this would also be a device with four planar electrodes 16 placed on the skin above the skeletal muscle of interest.

Figure 20:
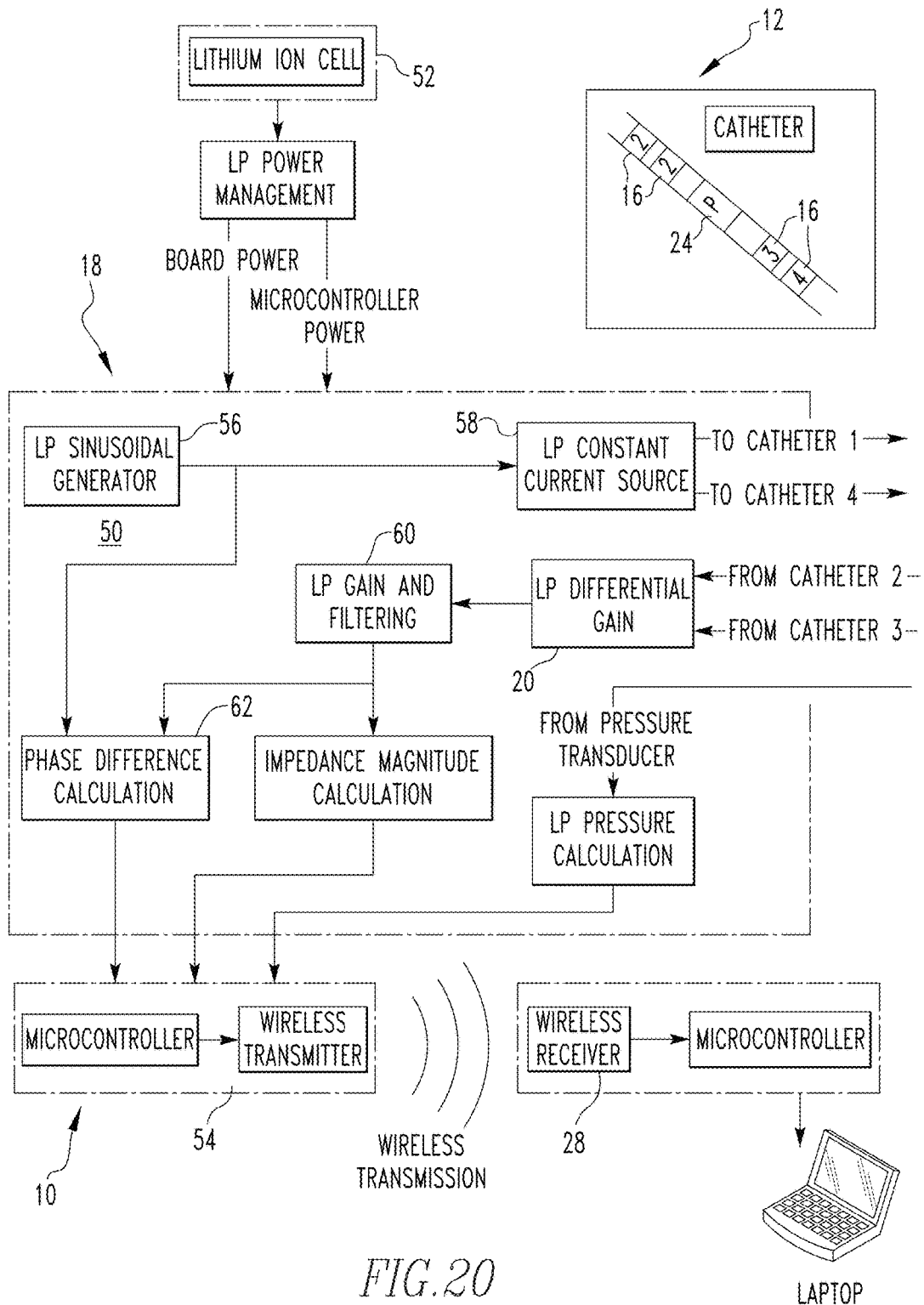
FIG. 20 is an overall block diagram of the apparatus of the present invention.

Referring now to FIG. 20, there is shown an apparatus 10 for monitoring an organ, such as the heart of a patient. The apparatus 10 comprises a detector 12 which detects the admittance of the organ. For the heart, this could be the heart's volume or diameter via admittance of the heart. The apparatus 10 comprises a transmitter 54 in communication with the detector 12 which transmits a wireless signal indicative of the admittance of the organ. For the heart, this could be the volume or the diameter of the heart.

The detector 12 may include a plurality of electrodes 16 in communication with the heart. The detector 12 may include a current source 18 in communication with at least one of the electrodes 16. The detector 12 may include a differential gain stage 20 in communication with at least one of the electrodes 16 which senses a differential voltage associated with the organ. The detector 12 may include a gain and filtering stage 60 in communication with the differential gain stage 20 which generates a DC signal corresponding to an amplitude of a resulting signal from the gain and filtering stage 60 to generate an impedance magnitude signal.

The apparatus 10 may include a phase detector 24 in communication with the organ which produces a phase signal associated with the heart muscle, if the organ is the heart, to allow removal of the heart muscle from the combined heart blood/muscle signal as detected with the admittance technique. The detector 12 may include a phase detector 62 in communication with at least one of the electrodes 16 which determines a phase difference between an original reference signal and a phase output signal from one of the electrodes 16 and produces a phase difference signal. The apparatus 10 may include a receiver 28 positioned remotely from the transmitter 54 and wherein the phase difference signal and amplitude signal derived from the heart blood volume are transmitted by the transmitter 54 wirelessly to the receiver 28. The receiver 28 may provide the wireless signal, which may include phase difference signal and an amplitude signal, it receives to a processor to process the signal.

In general, the transmitter 54 is placed where the majority of the hardware is located (usually proximal to the stimulation electrodes). For example, in a device which drains fluid into the abdomen via a shunt, the motor is placed in the abdomen. This is where the transmitter circuitry would be located. For burn victim skin, and for muscle edema, the transmitter is not necessary because both applications require external (skin surface) hardware. For the bladder, the transmitter could be either on the skin surface, or implanted within the bladder itself via the urethral orifice.

Some of these devices, especially skin and skeletal muscle (including the electrodes, both stimulating and sensing) would typically not be implanted at all. Thus, the associated circuitry is housed at an appropriate location outside of the patient. The bladder can be both implanted or external (the only organ which qualifies for both).

The present invention pertains to a method for monitoring an organ, such as the heart of a patient. The method comprises the steps of detecting with a detector 12 admittance of the organ, such as for a heart, the heart's volume or diameter via admittance. There is the step of transmitting with a transmitter 54 in communication with the detector 12 a wireless signal indicative of the admittance of the organ. For the heart, this could be the volume of the heart via admittance of the heart.

There may be the step of transmitting from the transmitter 54 wirelessly to a receiver 28 positioned remotely from the transmitter 54, a phase difference signal and an amplitude signal associated with the organ. For the heart, there may be the step of producing the heart volume signal 24 in communication with the heart. There may be the step of producing the phase difference signal and the amplitude signal from signals arising from electrodes 16 in communication with the heart.

The organ can be a lung and the transmitting step can include the step of transmitting with a transmitter 54 in communication with the detector 12 having electrodes 16 based on electrical signals derived from the lung a wireless signal indicative of the admittance of the lung.

The organ can be a bladder and the transmitting step can include the step of transmitting with a transmitter 54 in communication with the detector 12 having electrodes 16 based on electrical signals derived from the bladder a wireless signal indicative of the admittance of the bladder.

The organ can be a brain and the transmitting step can include the step of transmitting with a transmitter 54 in communication with the detector 12 having electrodes 16 based on electrical signals derived from the brain a wireless signal indicative of the admittance of the brain.

The organ can be a skeletal muscle and the transmitting step can include the step of transmitting with a transmitter 54 in communication with the detector 12 having electrodes 16 based on electrical signals derived from the skeletal muscle a wireless signal indicative of the admittance of the skeletal muscle.

The organ can be epidermis and the transmitting step can include the step of transmitting with a transmitter 54 in communication with the detector 12 having electrodes 16 based on electrical signals derived from the epidermis a wireless signal indicative of the admittance of the epidermis.

In the operation of the invention, FIG. 20 is an overall block diagram of the apparatus 10. A 3.7V, 625 mAh lithium ion-cell 52 is used to power the circuit. The circuit is based on a single-supply design with the clock generator, phase detector 26 chip, operational amplifiers and differential amplifiers operating on a single 3.6V supply. All the components were chosen with the lowest power possible while meeting the required voltage swings, bandwidth and slew-rate. To save area, quad-package low power operational amplifiers (LM6134) were used, wherever possible. The apparatus 10 included a backpack worn by the patient.

The backpack consisted of three different components. The instrumentation 50 on a surface mount PCB, the lithium-ion cell 52 and the microcontroller/transceiver 54 on a surface mount PCB.

The instrumentation 50 was interfaced with a tetrapolar PV catheter and the microcontroller/transceiver 54. The instrumentation PCB consisted of a low power (LP) 20-kHz sinusoid generator 56, followed by a LP voltage to current converter 58. This generated a 10 µA rms current, which fed to the outer two electrodes 16 of the catheter (Electrodes 1 and 4). The voltage resulting from the inner 2 electrodes (Electrodes 2 and 3) was then differentially sensed, followed by a gain and filtering stage 60. This was used to generate a DC signal corresponding to the amplitude of the resulting signal to generate an impedance magnitude signal. In parallel, a phase detection chip 62 was used to determine the phase difference between the original reference signal and the resulting output signal. A separate path was employed to process the pressure signal arising from the pressure transducer 24.

The resulting magnitude, phase and pressure signals were fed to the inputs of three 10-bit ADCs respectively (part of the LP microcontroller). A low power, low bit-rate protocol was used to transmit the signals over an RF link to the other transceiver. The receiver 28 was placed less than 6 feet away connected to a laptop. Data were collected and stored on this laptop for post-processing analysis and display.

The rat sized backpack shape and structure itself was determined based on the desire for it to be strong yet comfortable and light-weight. A simple and effective solution was to use a bubble wrap pocket to store the backpack contents. This was effective because the circuit was protected from any external fluids/influences and the wrap itself was comfortable and very light-weight.

Figure 30:
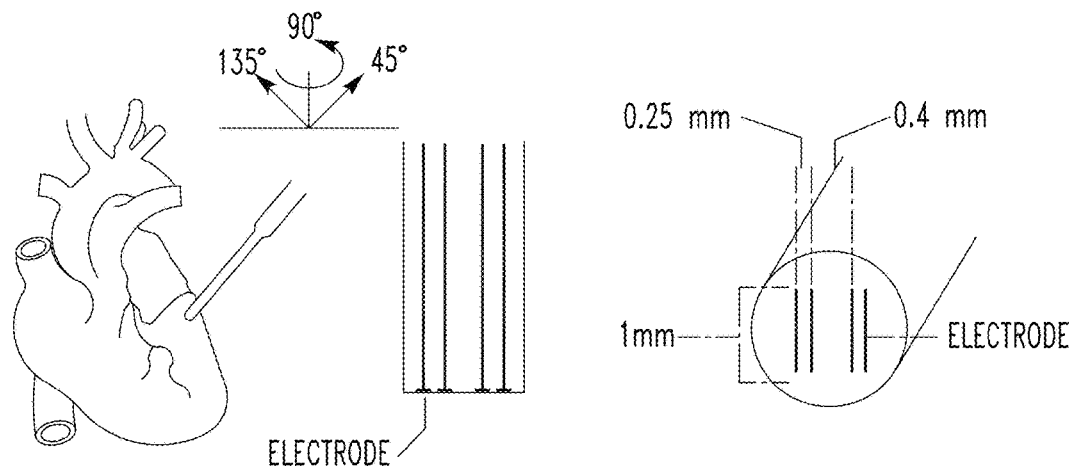
FIG. 30 shows an epicardial admittivity surface probe.
Figure 31:
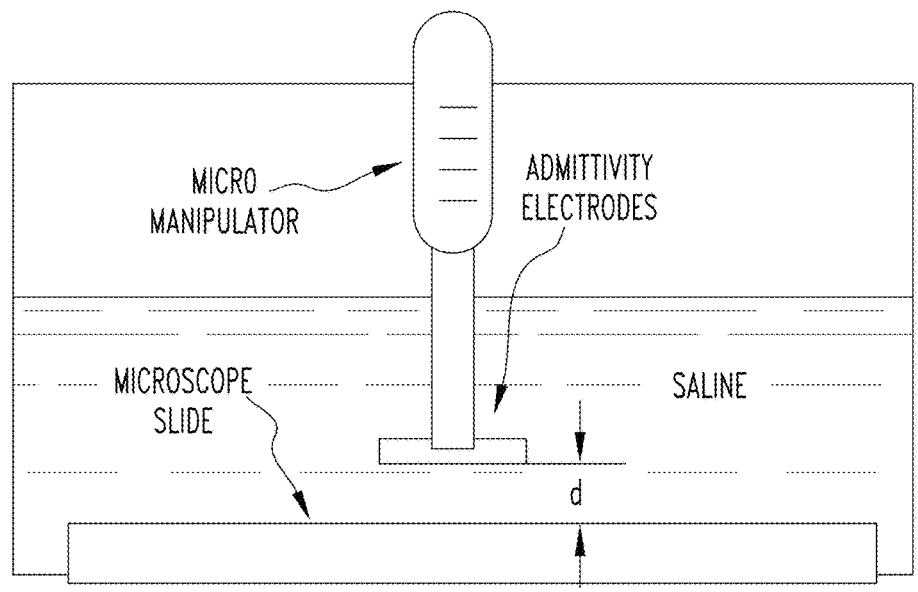
FIG. 31 shows the experimental setup to measure field penetration depth of surface catheters.

A miniature tetrapolar surface probe was applied to the epicardial surface of the beating murine heart in vivo [FIG. 30]. The probe contains four parallel platinum electrodes aligned with an intra-electrode spacing of 0.25, 0.4, and 0.25 mm between electrodes 1 and 2, 2 and 3, and 3 and 4, respectively. In the standard tetrapolar technique electrodes 1 and 4 are driven with a current source and electrodes 2 and 3 are used for potential measurement at negligible current (due to the high input impedance of the voltage sensing differential amplifier). The tetrapolar method is thus essentially insensitive to the series electrode-electrolyte interface impedance of the measurement electrodes. A similar configuration was applied to the beating rat heart in vivo as well. FIG. 31 shows the experimental setup to measure field penetration depth of surface catheters.

The electrode design was modeled after an electrode developed for the canine heart by Steendijk et al. However, their electrode spacing was designed to sample only the epicardium. Effectively wider electrode spacings relative to the myocardial thickness were used here to gain a greater depth of penetration by the electric field. This minimizes the effect of tissue anisotropy in the "longitudinal plane", as it were, by measuring over a substantial fraction of the ventricular free wall thickness. Consequently, the effect of anisotropy due to fiber orientation within layers of myocardium is averaged. It was confirmed (by measurement at four different orientations of 0, 45, 90 and 135 degrees) that probe orientation effects showed no variation more significant than intra-measurement and inter-animal variability.

Figure 21:
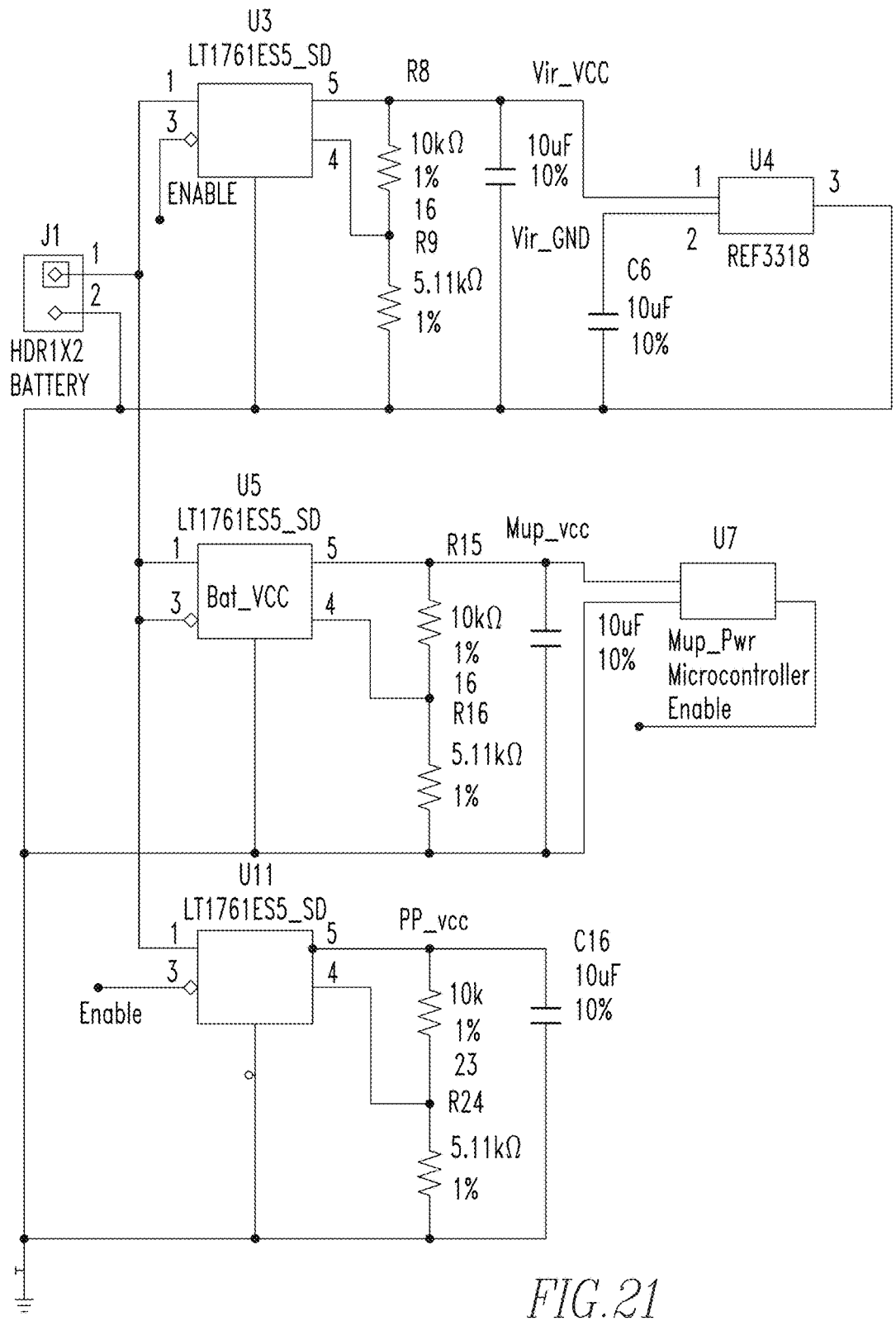
FIG. 21 shows power management blocks.

The entire circuit was powered of a single 3.7V, 625 mAh lithium-ion cell. The instrumentation was designed to run off a single power supply (3.6V). Therefore, apart from the actual ground (0V), there was an additional virtual ground set at 1.8V. FIG. 21 is the setup of the power management circuit. All resistors used are precision metal-film resistors (1% tolerance) and all capacitors are ceramic capacitors (10% tolerance).

Three different LP voltage regulators (LT1761ES5-SD) were used to power different parts of the backpack. All of them were set at a 3.6V level. The regulator U5 powers the microcontroller/transmitter 54. This was always ON. This way the microcontroller would always receive power, regardless of whether the instrumentation is collecting data or it is in an idle state. The regulator U11 powers the phase detector 26 chip and also serves as the voltage difference applied across the bridge that is part of the pressure sensing network. The regulator U3 powers the rest of the instrumentation (LP clock, LP operational amplifiers and LP differential amplifiers). Both U11 and U3 are controlled by an enable signal, which is connected to the microcontroller. It is ON for the time frame when the instrumentation is actively sending data to the microcontroller (about 12 seconds every 2 minutes). It is OFF for the rest of the duration of the 2 minutes, thus, conserving power. The virtual analog ground (1.8V) connection is provided using a LP reference chip (U4 REF3318).

Figure 22:
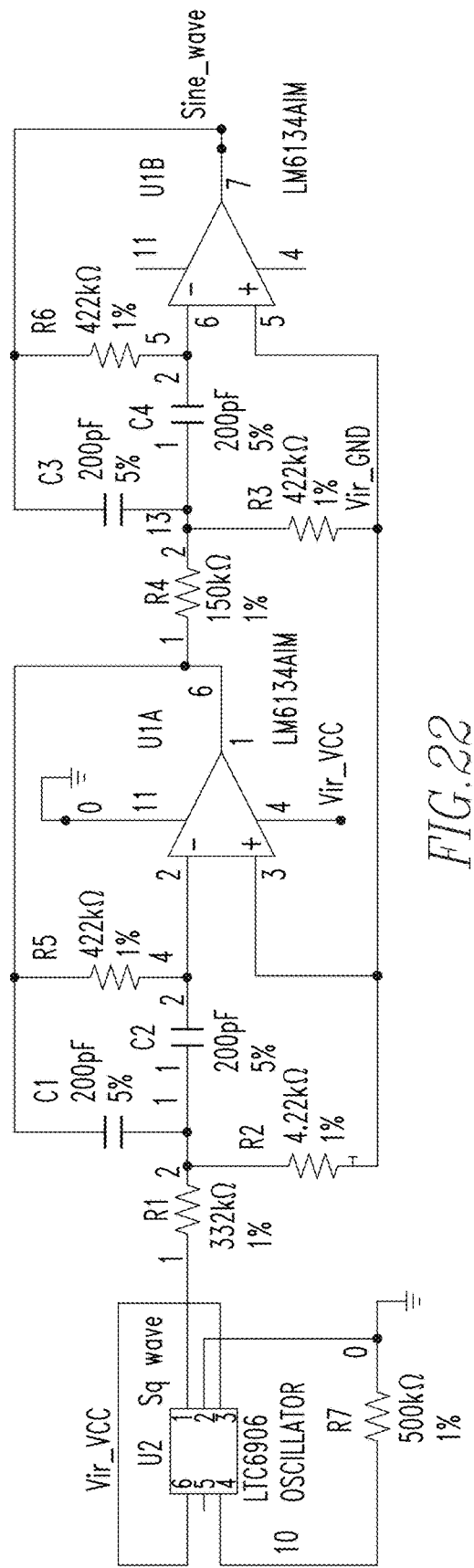
FIG. 22 shows a low power sinusoidal generator.

FIG. 22 is the circuit implementation of the LP sinusoidal generator. A LP oscillator (LTC6906) was used to generate a reference square wave at 20 kHz. This was followed by a 20 kHz band pass filter implemented as 2 biquad sections with Sallen-Key Multiple Feedback architecture. The output is a 1Vp-p sine wave at 20 kHz, relative to the virtual analog ground at 1.8 V. This would be used as the reference signal for the phase detector 26 chip. The node "0" in all the circuit diagrams refers to the "real" power ground (0V). All resistors used are precision metal-film resistors (1% tolerance) and all capacitors are ceramic capacitors (10% tolerance).

Figure 23:
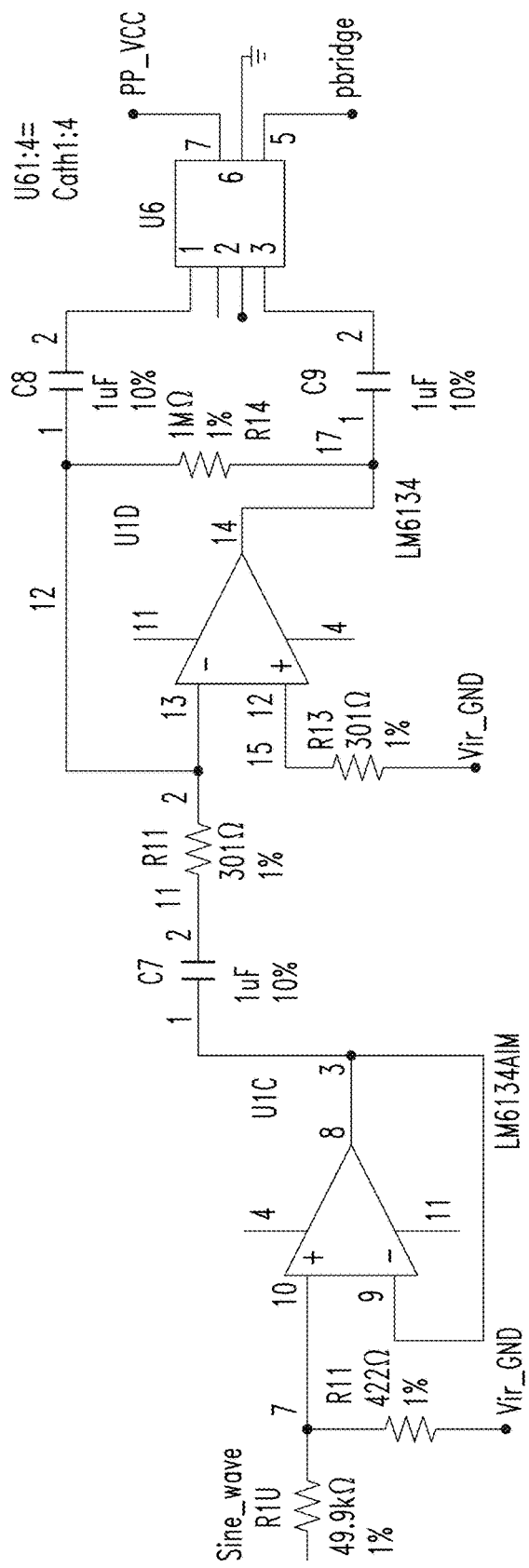
FIG. 23 shows a low power constant current source.

FIG. 23 illustrates the circuit used for building of the constant current source 18. The 1 MΩ resistor in the feedback path of the operational amplifier guarantees that it never enters an open loop state. The 1 μF capacitors in series with the signal path provide a means for the DC elimination from the AC sinusoidal stimulus signal entering the catheter (the heart). Additional elimination of the extremely low frequency signals (close to DC) is provided by the pass high pass pole provided by the C7-R12 combination. The node "0" in all the circuit diagrams refers to the "real" power ground (0V). All resistors used are precision metal-film resistors (1% tolerance) and all capacitors are ceramic capacitors (10% tolerance).

Figure 24:
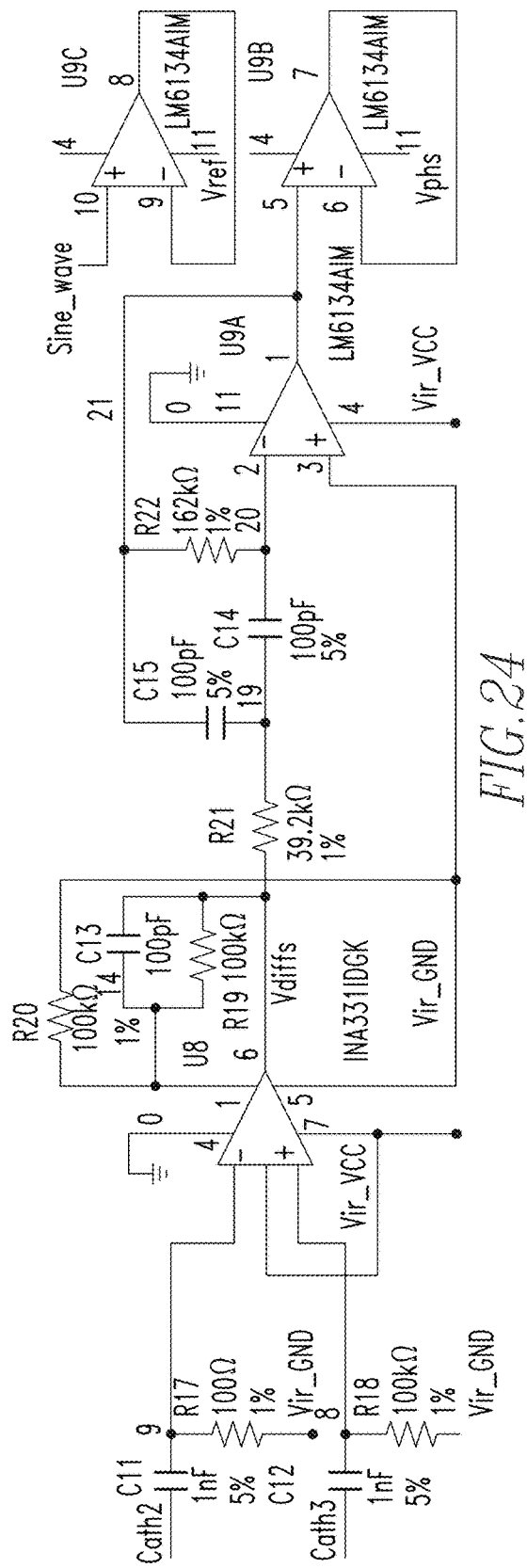
FIG. 24 shows low power post-catheter signal processing.

The differential signal from the inner two electrodes 16 of the catheter is processed by a differential gain stage 20. A low power instrumentation amplifier (INA331IDGK) was used with a gain of 10V/V shown in FIG. 24. This was followed by a 20 kHz band pass filter (Q=1, Sallen Key Multiple Feedback architecture). This is followed by a gain stage and buffering. The output is the phase shifted, amplitude modified signal used for impedance magnitude calculation. This also serves as the second input for the phase detector 26 chip. The node "0" in all the circuit diagrams refers to the "real" power ground (0V). All resistors used are precision metal-film resistors (1% tolerance) and all capacitors are ceramic capacitors (10% tolerance).

Figure 25:
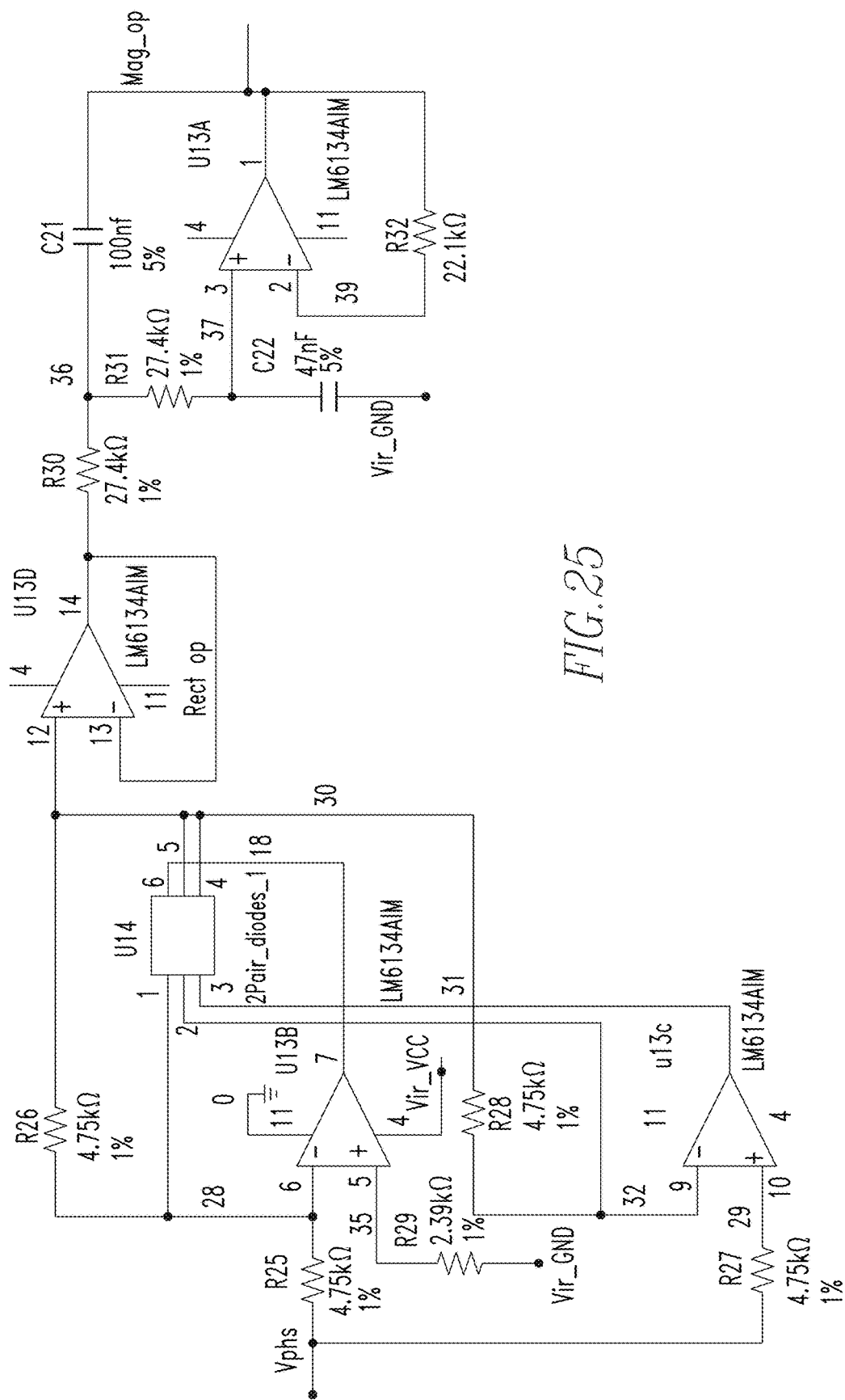
FIG. 25 shows impedance magnitude calculation.

The impedance magnitude calculation circuit is illustrated in FIG. 25. This essentially is a full wave rectification stage followed by a low pass filter at 25 Hz (Q=0.5803, Sallen-Key Multiple feedback architecture). U14 is a single chip package containing 2 pair of diodes. This is convenient because it was customized for rectifier circuits, thereby, reducing area.

Figure 26:
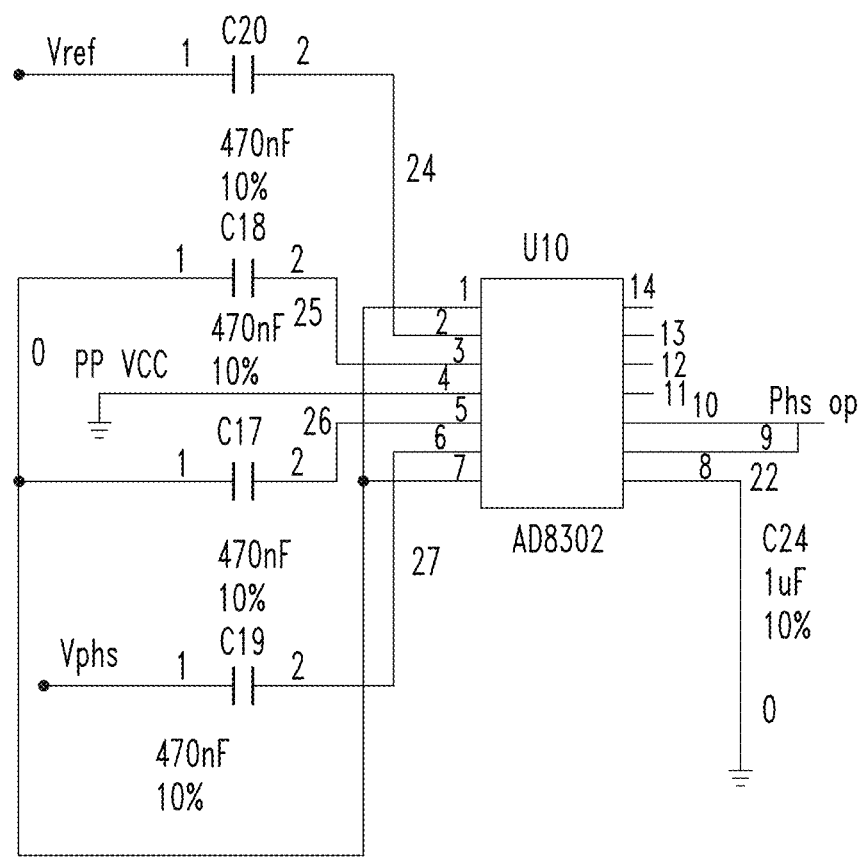
FIG. 26 shows low power phase estimation.

To obtain the phase difference between the reference voltage signal and the phase shifted post-processed signal, a RF/IF Phase detector 26 chip (AD8302) was used in the low-frequency" topology, as shown in FIG. 26.

Figure 27:
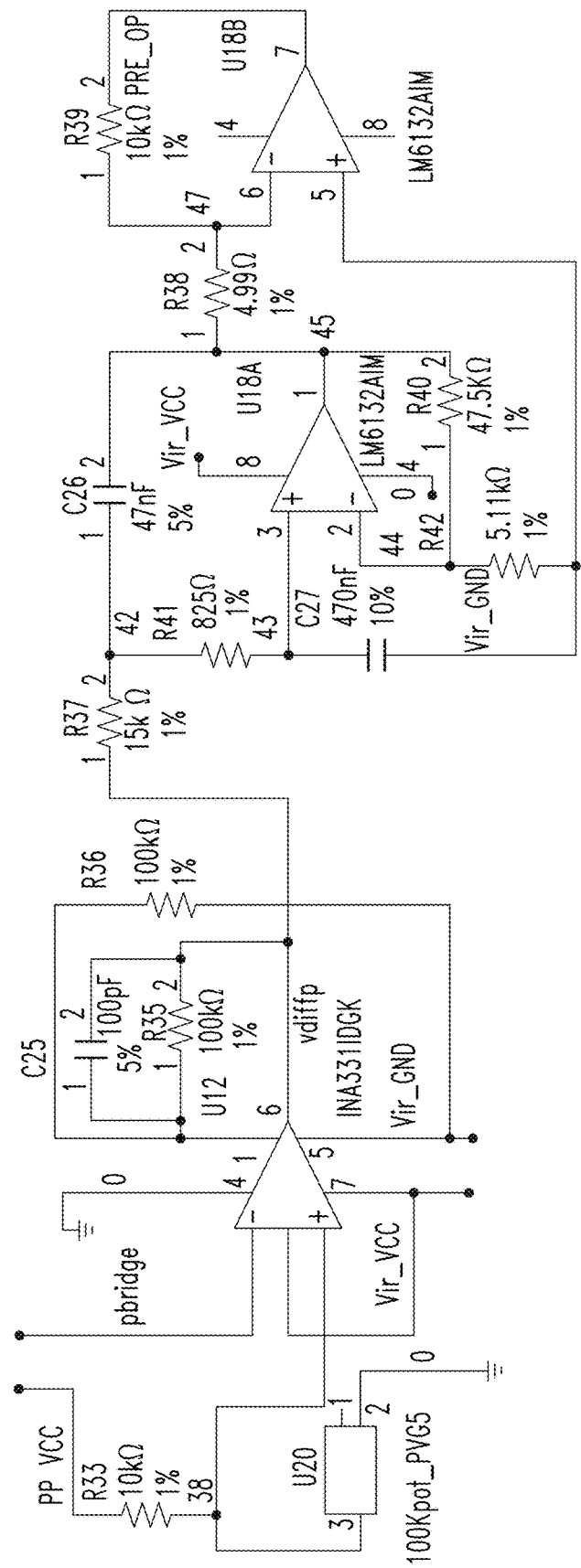
FIG. 27 shows low power pressure calculation.

FIG. 27 illustrates the schematic designed for the LP pressure calculation. Two arms of the Wheatstone bridge are part of the pressure transducer 24. The remaining two arms are completed using a resistor network. The regulator supplies a constant voltage (3.6V) across the bridge. The differential voltage is sensed using the LP instrumentation amplifier (INA331IDGK), followed by low pass filter (25 Hz, Q=0.52, Sallen-Key Multiple feedback architecture) and a gain stage.

A 4-layer PCB was made using the above schematics. To save on area, all the four layers were dedicated to signals. The final PCB outline came to about 1.78"×1.54".

Figure 28:
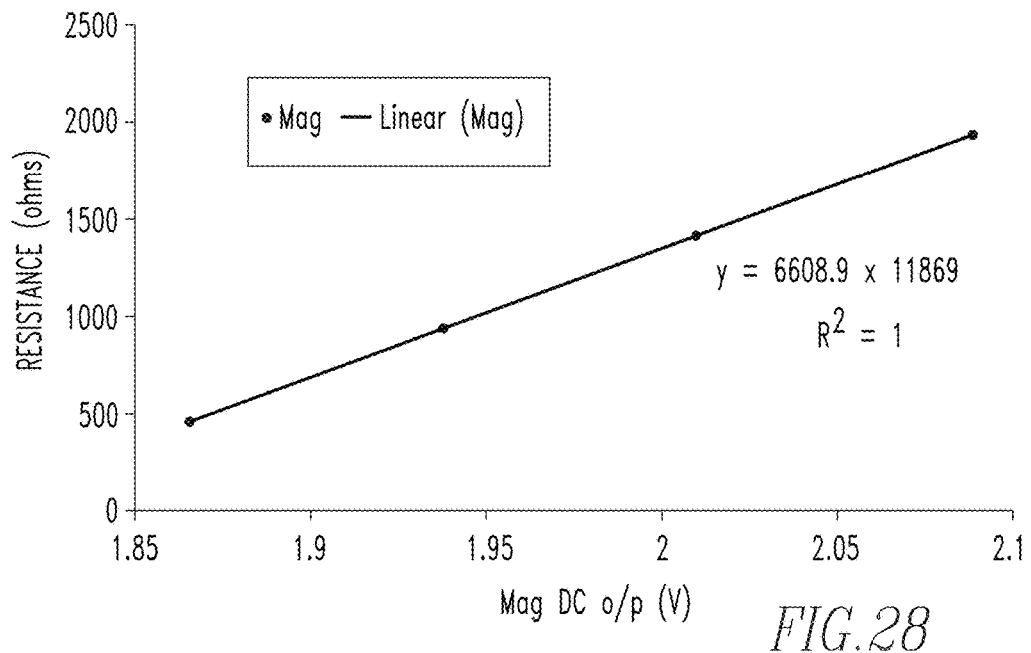
FIG. 28 shows an impedance magnitude calibration curve.

To calibrate the impedance magnitude, four known precision resistors were connected as the test load (in place of the catheter). The resistor itself was placed between Electrodes 2 and 3 and Electrode 1 was shorted to Electrode 2 and similarly Electrode 4 was shorted with Electrode 3. Thus, this represented a purely resistive load. The resistors were chosen to represent the entire range of impedance magnitudes that can be expected from a rat LV PV experiment. The resistors themselves were 1% metal-film resistors. FIG. 28 is a representative impedance magnitude calibration curve obtained from the rat backpack instrumentation.

Figure 29:
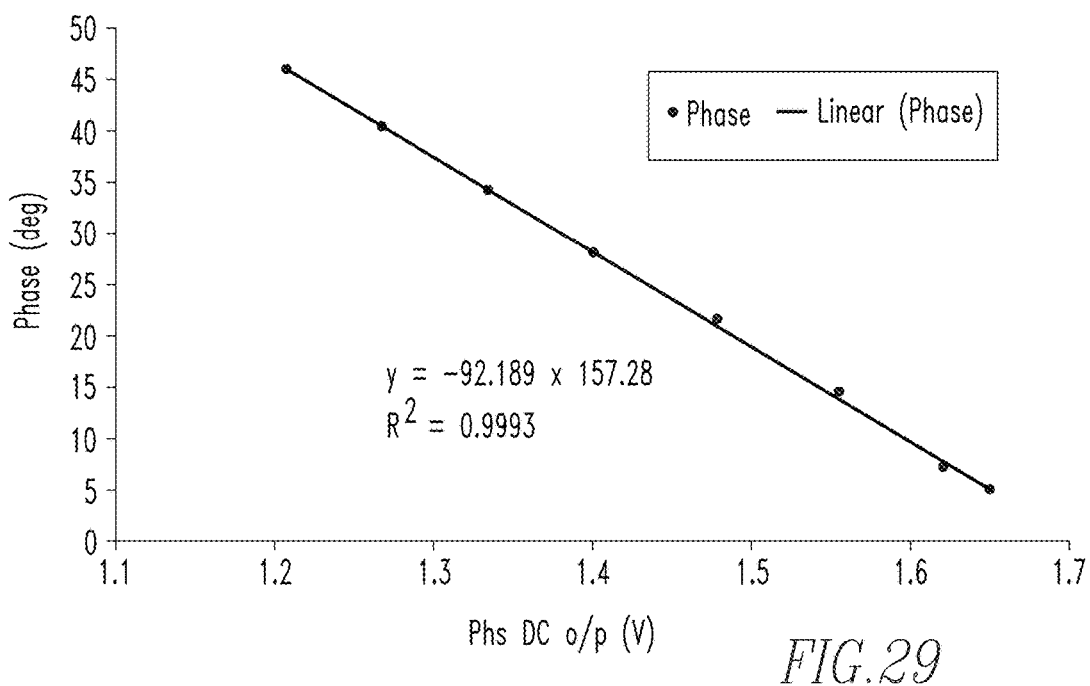
FIG. 29 shows a phase calibration curve.

To calibrate the phase detection chip, known parallel R-C load combinations were connected as the test load (in place of the catheter). The introduced phase difference was calculated at f=20 kHz. FIG. 29 is a representative phase calibration curve obtained from the backpack instrumentation.

In order to eliminate the effects of the catheter, the catheter is connected to the circuit. The electrodes 16 are then submerged into saline solutions of known conductivity. Table 1 represents a typical saline calibration table.

TABLE 1

Saline calibration table

| Cond. (uS/cm) | Mag (Ω) | Phs (deg) | MagY (S) | MagY (μS) | F (cm) | F (m) | K (1/m) | K (1/cm) | ImY (μS) | ReY (μS) |
|---|---|---|---|---|---|---|---|---|---|---|
| 1025 | 1620 | 18.0 | 0.000617 | 617 | 0.573 | 0.00573 | 175 | 1.75 | 191 | 587 |
| 1882 | 1341 | 15.8 | 0.000746 | 746 | 0.381 | 0.00381 | 262 | 2.62 | 204 | 718 |
| 2860 | 632 | 6.5 | 0.001582 | 1582 | 0.550 | 0.00550 | 182 | 1.82 | 180 | 1572 |
| 3540 | 610 | 6.1 | 0.001639 | 1639 | 0.460 | 0.00460 | 217 | 2.17 | 175 | 1630 |
| 5690 | 481 | 4.0 | 0.002079 | 2079 | 0.365 | 0.00365 | 274 | 2.74 | 145 | 2074 |
| | | | | | Avg | 0.00466 | 215 | | | |

Where Cond. is the conductivity of the saline solution, Mag is the impedance magnitude measured using the backpack, Phs is the measured phase using the backpack, MagY is the admittance magnitude, F is the field form factor and K is the probe constant. F and K are estimated from the real part of admittance (ReY) and the conductivity of the saline solution (Raghavan, K., Porterfield, J. E., Kottam A. T. G., Feldman, M. D., Escobedo, D., Valvano, J, W., and Pearce, J. A., *Electrical conductivity and permittivity of murine myocardium*. IEEE Trans Biomed Eng, (Accepted, In Press), 2009.). ImY represents the imaginary component of the admittance. This table's contents would be used in the conversion of the LV admittance data into volume using Wei's equation (Raghavan, K., Porterfield, J. E., Kottam A. T. G., Feldman, M. D., Escobedo, D., Valvano, J, W., and Pearce, J. A., *Electrical conductivity and permittivity of murine myocardium*. IEEE Trans Biomed Eng, (Accepted, In Press), 2009).

To simulate the beating of the heart, the backpack circuit was tested for dynamic characteristics. To simulate the changing magnitude of impedance, an amplitude-modulated (AM) signal was applied. The amplitude varied at a rate of 5 Hz (300 beats/minute) riding over a 20 KHz stimulus. To test the phase variation, the reference signal at 20 kHz was generated along with a phase modulated signal at a rate of 4 Hz (240 beats/minute) over the same stimulus signal at 20 kHz. These two signals were created in LabVIEW™ (National Instruments (NI), Austin, Tex.) and output via the DAC channels of a fast sampling ADC (NI PCI-6110, 5 MS/s/channel) capable of outputting up to 2.5 MS/s on two simultaneous 16-bit, analog output channels.

To estimate the battery life, the 3.7V lithium-ion cell rated at 625 mAh was connected to the circuit and the circuit was allowed to run for more than 24 hours. Current data was collected using Chart during the entire time at a rate of 1 Hz. Table 2 summarizes the results.

beats/min (2.5 Hz) to about 300 beats/min (5 Hz). Therefore, the signals that have to be transmitted are of a very low frequency content (<5 Hz). Therefore, the required data rate is very low.

The Texas Instruments' (TI) eZ430-RF2500 kit was ideal for this application (Texas Instruments, Dallas, Tex.). This was a complete kit with a MSP430F2274 microcontroller and CC2500 2.4 GHz wireless transceiver. The key points which motivated this choice were:

a) The MSP430F2274 microcontroller was ultra-low power drawing a maximum active (ON) current of 390 μA. In the standby (OFF) mode, it draws a maximum current of 1.4 μA.
b) The microcontroller had 8 10-bit, 200 ksps SAR ADCs for use.
c) The CC2500 transceiver was also of the low power type with programmable data rates from 1.2 to 500 kbps drawing a typical current of 21.2 mA during TX.
d) Ultra low power star network stack called as SimpliciTI™ protocol.
e) Easily programmable/debuggable with convenience of USB. Sample code already was setup to transmit and receive low data rate temperature sensor data.

TABLE 2

Battery life estimation

| Current type | Current (mA) | Bkpk. Reg. | Bkpk. | Mic. Reg. | Mic. | Mic. State | ADC | TxRx | Duration (s) | Avg. current mA/hr. |
|---|---|---|---|---|---|---|---|---|---|---|
| Bkpk. ON current | 41.6 | ON | ON | ON | ON | LPM0 | ON | ON | 360 | 4.16 |
| Bkpk. OFF current | 22.3 | OFF | OFF | ON | ON | LPM3 | OFF | OFF | 3240 | 20.07 |
| | | | | | | | | | Total | 24.23 |
| | | | | | | | | | Battery life (hrs.) | 25.8 |

In Table 2, "Mic." refers to the microcontroller, "TxRx" refers to the transceiver, "LPM" refers to Low Power Mode of the microcontroller, and "Bkpk." refers to backpack. The results show that the battery can last for 25.8 hours. Experimental results also prove the same.

Table 3 summarizes the weight of the individual components making up the backpack.

TABLE 3

Backpack weight distribution

| Item | Weight (g) | % of weight |
|---|---|---|
| Instrumentation PCB weight | 7.49 | 27.0 |
| Mup + TxRx PCB weight | 1.77 | 6.4 |
| Total circuit weight | 9.26 | |
| Li ion cell weight | 18.5 | 66.7 |
| Backpack weight | 27.8 | |

The choice of wireless telemetry was critical because the battery needs to power the microcontroller/TX pair. Therefore, it has to be low power. Also, the patient's (or rat for these actual experiments) heart rate varies from about 150

TABLE 1

Terminology:

Ohm's law: $V = IR$ where V is voltage, I is current, and R resistance, alternatively $I = VG$ where G is conductance.
Conductance, or G (S)
Conductivity, or σ (S/m)
Resistance, or R (ohm, Ω) = 1/conductance
Resistance of myocardium or muscle = $R_m$
Resistance of blood = $R_b$
Resistivity, or ρ (Ω x m) = 1/conductivity
Admittance (Complex Conductance), or $Y = I/V$
= G (real) + jB
 (imaginary), where G = conductance, j = square root of −1,
 $B = \omega C$. $\omega = 2\pi f$ (f = frequency), C = capacitance. Used for tissues in parallel.
Capacitance of myocardium or muscle = $C_m$
Capacitance of the catheter and instrumentation = $C_c$
Magnitude $|Y| = \sqrt{(G^2 + B^2)}$, and Phase angle (θ)
 = $\tan^{-1}$ (B/G),
 where B and G are defined above.
Impedance (Complex Resistance), or $Z = V/I$ =
R (real) + jX TABLE 1-continued Terminology:

(imaginary), where R = resistance and X = 1/wC. Used for tissues in series.
Magnitude |Z| = √(R² + X²), and Phase angle (θ) = tan⁻¹ (X/R),
where X and R are defined above.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. An implanted device for an organ of a patient comprising:
a housing;
a detector having electrodes that have a varying distance over time between them which produces a detector signal based on electrical signals derived from the organ;
a signal processor disposed in the housing in communication with the detector which determines admittance from the detector signal based on the varying distance over time between the electrodes; and
a drive circuit disposed in the housing to cause the electrodes to generate emitted electrical signals, the detector that generates the detector signal based on electrical signals derived from tissue and fluid from the organ; and the signal processor in communication with the detector which subtracts in real time a tissue component from the detector signal and produces a fluid volume signal, the electrodes produce a combined signal that has a tissue component and a fluid component.

2. The implanted device as described in claim 1 wherein the fluid is blood, the tissue is myocardium and the processor determines LV, RV, LA, or RV length, area, and/or volume of the heart in 1, 2 or 3 dimensions.

3. The implanted device as described in claim 2 wherein the myocardial component Rm is determined by $$R_m = \frac{-\text{Im}\{\overline{Z}\} \times \left(1 + \left(\frac{\omega \varepsilon_m}{\sigma_m}\right)^2\right)}{\frac{\omega \varepsilon_m}{\sigma_m}},$$

where $\overline{Z}$ is the complex impedance; $\omega = 2\pi f$ where f is the frequency; $\varepsilon_m$ is permittivity of muscle; and $\sigma_m$ is the conductivity of muscle.

4. The implanted device as described in claim 3 wherein the fluid is blood and blood component Rb is determined by $$R_b = \text{Re}\{\overline{Z}\} - \frac{R_m}{1 + (\omega R_m C_m)^2},$$

where $\overline{Z}$ is the complex impedance; $\omega = 2\pi f$ where f is the frequency; $R_m$ is the resistance of muscle, and $C_m$ is the capacitance of muscle.

5. The implanted device as described in claim 4 wherein the signal processor subtracts in real time the myocardial component from the detector signal and produces the left and right ventricle, and left and right atrial blood volume signal.

6. An implanted device for an organ of a patient comprising:
a housing;
a detector having electrodes that have a varying distance over time between them which produces a detector signal based on electrical signals derived from the organ;
a signal processor disposed in the housing in communication with the detector which determines admittance from the detector signal based on the varying distance over time between the electrodes; and
a drive circuit disposed in the housing to cause the electrodes to generate emitted electrical signals, the detector that generates the detector signal based on electrical signals derived from tissue and fluid from the organ, the signal processor in communication with the detector which subtracts in real time a tissue component from the detector signal and produces a fluid volume signal, the electrodes produce a combined signal that has a tissue component and a fluid component, the fluid is blood, the tissue is myocardium and the processor determines LV, RV, LA, or RV length, area, and/or volume of the heart in 1, 2 or 3 dimensions, the myocardial component Rm is determined by $$R_m = \frac{-\text{Im}\{\overline{Z}\} \times \left(1 + \left(\frac{\omega \varepsilon_m}{\sigma_m}\right)^2\right)}{\frac{\omega \varepsilon_m}{\sigma_m}},$$

where $\overline{Z}$ is the complex impedance; $\omega = 2\pi f$ where f is the frequency; $\varepsilon_m$ is permittivity of muscle; and $\sigma_m$ is the conductivity of muscle.

* * * * *